(12) United States Patent
Fasano et al.

(10) Patent No.: US 9,279,807 B2
(45) Date of Patent: Mar. 8, 2016

(54) MATERIALS AND METHODS FOR THE TREATMENT OF CELIAC DISEASE

(75) Inventors: Alessio Fasano, West Friendship, MD (US); Blake Paterson, Baltimore, MD (US)

(73) Assignees: ALBA THERAPEUTICS CORPORATION, Baltimore, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 994 days.

(21) Appl. No.: 13/214,857

(22) Filed: Aug. 22, 2011

(65) Prior Publication Data

US 2012/0076861 A1 Mar. 29, 2012

Related U.S. Application Data

(63) Continuation of application No. 11/955,522, filed on Oct. 26, 2007, now Pat. No. 8,034,776.

(60) Provisional application No. 60/854,459, filed on Oct. 26, 2006, provisional application No. 60/865,236, filed on Nov. 10, 2006.

(51) Int. Cl.

| | |
|---|---|
| *A61K 9/16* | (2006.01) |
| *A61K 39/00* | (2006.01) |
| *A61K 38/08* | (2006.01) |
| *A61K 38/12* | (2006.01) |
| *C07K 17/00* | (2006.01) |
| *G01N 33/564* | (2006.01) |
| *G01N 33/84* | (2006.01) |

(52) U.S. Cl.
CPC .............. *G01N 33/564* (2013.01); *A61K 38/08* (2013.01); *G01N 33/84* (2013.01); *G01N 2333/5412* (2013.01); *G01N 2333/57* (2013.01)

(58) Field of Classification Search
CPC . A61K 38/08; G01N 33/564; G01N 2333/57; G01N 2333/5412; G01N 33/84
USPC ........ 424/490, 185.1; 514/21.7; 530/328, 300
See application file for complete search history.

(56) References Cited

U.S. PATENT DOCUMENTS

| | | | |
|---|---|---|---|
| 5,827,534 A | 10/1998 | Fasano | |
| 5,864,014 A | 1/1999 | Fasano | |
| 5,912,323 A | 6/1999 | Fasano | |
| 5,945,510 A | 8/1999 | Fasano | |
| 5,948,629 A | 9/1999 | Fasano | |
| 6,458,925 B1 | 10/2002 | Fasano | |
| 6,506,577 B1 | 1/2003 | Deming et al. | |
| 6,670,448 B2 | 12/2003 | Fasano | |
| 6,733,762 B1 | 5/2004 | Fasano et al. | |
| 6,793,936 B2 | 9/2004 | Devane et al. | |
| 6,936,689 B2 | 8/2005 | Fasano | |
| 7,026,294 B2 | 4/2006 | Fasano et al. | |
| 7,189,696 B2 | 3/2007 | Fasano | |
| 7,294,689 B2 | 11/2007 | Fasano et al. | |
| 7,531,504 B2 | 5/2009 | Fasano | |
| 7,531,512 B2 | 5/2009 | Fasano et al. | |
| 7,582,603 B2 | 9/2009 | Fasano | |
| 8,034,776 B2 * | 10/2011 | Fasano et al. ................ 514/21.7 |
| 8,183,211 B2 | 5/2012 | Fasano | |
| 2003/0152627 A1 | 8/2003 | Beckert et al. | |
| 2003/0180352 A1 | 9/2003 | Patel et al. | |
| 2005/0249807 A1 | 11/2005 | Brown et al. | |
| 2006/0269968 A1 | 11/2006 | Fasano | |
| 2007/0196501 A1 | 8/2007 | Paterson et al. | |
| 2008/0103100 A1 | 5/2008 | Fasano et al. | |
| 2009/0069247 A1 | 3/2009 | Paterson et al. | |

FOREIGN PATENT DOCUMENTS

| | | |
|---|---|---|
| EP | 0 557 897 | 9/1993 |
| EP | 0 675 199 | 10/1995 |
| JP | 2004-517156 | 6/2004 |
| WO | 97/33909 | 9/1997 |
| WO | WO9837096 | 8/1998 |
| WO | WO9852415 | 11/1998 |
| WO | WO 00/07609 | 2/2000 |
| WO | WO0189551 | 11/2001 |
| WO | WO2004004696 | 1/2004 |
| WO | 2005/010022 | 2/2005 |

OTHER PUBLICATIONS

Fasano, "Biological Perspectives: Physiological, Pathological, and Therapeutic Implications of Zonulin-Mediated Intestinal Barrier Modulation—Living Life on the Edge of the Wall", The American Journal of Pathology, Nov. 2008, vol. 173, No. 5, pp. 1243-1252.

Pizzuti et al., "Transcriptional downregulation of tight junction protein ZO-1 in active coeliac diseas is reversed after a gluten-free diet", Digestive and Liver Disease, May 2004, vol. 36(5), pp. 337-341.

Fasano et al., "The Role of the Intestinal Barrier Function in the Pathogenesis of Celiac Disease—Frontiers in Celiac Disease". Pediatric Adolescent Medicine Basel, Karger, 2008, vol. 12, pp. 89-98.

Fasano, "Surprises from Celiac Disease", Scientific American, Aug. 2009, vol. 301(2), pp. 54-61.

Clayburgh et al., "A porous defense: the leaky epithelial barrier in intestinal disease", Laboratory Investigation, 2004, vol. 84, pp. 282-291.

Wang et al., "Human zonulin, a potential modulator of intestinal tight junctions", Journal of Cell Science, 2000, vol. 113, pp. 4435-4440.

Holmes et al., "Claudin profiling in the mouse during postnatal intestinal development and along the gastrointestinal tract reveals complex expression patterns", Gene Expression Patterns, 2006, vol. 6, pp. 581-588.

(Continued)

*Primary Examiner* — Ganapathirama Raghu

(74) *Attorney, Agent, or Firm* — Morgan, Lewis & Bockius LLP

(57) ABSTRACT

The present invention provides materials and methods for the treatment of celiac disease. In addition, the present invention provides materials and methods of monitoring the treatment of a subject having celiac disease.

8 Claims, 17 Drawing Sheets

(56) References Cited

OTHER PUBLICATIONS

Murray, "The widening spectrum of celiac disease", Am. J. Clin. Nutr., 1999, vol. 69, pp. 354-365.
Chiarioni et al., "Gluten-Free Diet Normalizes Mouth-to-Cecum Transit of a Caloric Meal in Adult Patients with Celiac Disease", Digestive Diseases and Sciences, Oct. 1997, vol. 42, No. 10, pp. 2100-2105.
Deli, "Potential use of tight junction modulators to reversibly open membranous barriers and improve drug delivery", Biochemica et Biophysica Acta, 2009, 1788, pp. 892-910.
Fasano et al., "Zonulin, a newly discovered modulator of intestinal permeability, and its expression in coeliac disease", The Lancet, Apr. 2000, vol. 355, pp. 1518-1519.
Ewe et al., "Inflammation Does Not Decrease Intraluminal pH in Chronic Inflammatory Bowel Disease", Digestive Diseases and Sciences, Jul. 1999, vol. 44, No. 7, pp. 1434-1439.
Sadik et al., "Gut Transit in Celiac Disease: Delay of Small Bowel Transit and Acceleration after Dietary Treatment", American Journal of Gastroenterology, Dec. 2004, vol. 99, No. 12, pp. 2429-2436.
McConnell et al., "Gut instincts: Explorations in intestinal physiology and drug delivery", International Journal of Pharmaceutics, Dec. 2008, vol. 364, No. 2, pp. 213-226.
Sapone et al., "Zonulin Upregulation Is Associated With Increased Gut Permeability in Subjects With Type 1 Diabetes and Their Relatives", Diabetes, May 2006, vol. 55, pp. 1443-1449.
Watts et al., "Role of the intestinal tight junction modulator zonulin in the pathogenesis of type 1 diabetes in BB diabetic-prone rats", PNAS, Feb. 2005, vol. 102, No. 8, pp. 2916-2921.
Di Sabatino et al., "Coeliac Disease", The Lancet, Apr. 2009, vol. 373, pp. 1480-1493.
Fasano et al., "Mechanisms of Disease: the role of intestinal barrier function in the pathogenesis of gastrointestinal autoimmune diseases", Nature Clinical Practice Gastroenterology & Hepatology, Sep. 2005, vol. 2, No. 9, pp. 416-422.
Arhewoh et al., "Optimising oral systems for the delivery of therapeutic proteins and peptides", African Journal of Biotechnology, Dec. 2005, vol. 4(13), pp. 1591-1597.
Ciccocioppo et al., "Altered Expression, Localization, and Phosphorylation of Epithelial Junction Proteins in Celiac Disease", American Journal of Clinical Pathology, 2006, vol. 125, pp. 502-511.
Drago et al., Gliadin, zonulin and gut permeability: Effects on celiac and non-celiac intestinal mucosa and intestinal cell lines, Scand.J. Gastroenterol., 2006, vol. 41: 408-419.
Clemente et al., "Early effects of gliadin on enterocyte intracellular signalling involved in intestinal barrier function", Gut, 2003, vol. 52, pp. 218-223.
Teahon et al., "Assessing the site of increased intestinal permeability in coeliac and inflammatory bowel disease", Gut, 1996, vol. 38, pp. 864-869.
Baudry et al., "Cloning of a Gene (zot) Encoding a New Toxin Produced by Vibrio cholerae", Infection and Immunity, Feb. 1992, vol. 60, No. 2., pp. 428-434.
Bolton et al., "Loss of the tight junction proteins occludin and zonula occludens-1 from cerebral vascular endothelium during neutrophil-induced blood-brain barrier breakdown in vivo", 1998, Neuroscience, vol. 86, No. 4, pp. 1245-1257.
International Search Report Issued in PCT/US07/82720 on Aug. 1, 2008, 8 pages.
Clemente et al., Gastroenterology, 126(4), Suppl. 2, p. A249 (Apr. 2004).
Fasano, A. et al., "Zonulin and its regulation of intestinal barrier function: the biological door to inflammation, autoimmunity, and cancer," Physiological Reviews, 91:151-175 (2011).
"Ileum," Wikipedia, Retrieved from the Internet: <http://en.wikipedia.org/wiki/ileum>, Retrieved on Oct. 11, 2012, 4 pages.
Rohm Deguss-Huls Group News, Pharma Polymers, Oct. 2000, No. 7, pp. 1-6.
Thoma, K. et al, "The solubility kinetics of enteric-resistant tablets using riboflavin test tablets. 6. Pharmaceutic-technologic and analytic studies on gastric juice-resistant dosage forms," Pharmazine, 46(5):331-336 (1991) (with English Abstract).
Tripathi, A. et al, "Identification of human zonulin, a physiological modulator of tight junctions, as prehaptoglobin-2," PNAS, 106(39):16799-16804 (2009).
Vantini, I. et al, "In vitro study of a new pancreatic enzyme with high lipase content in enteric coated microtablets," Clinica Terapeutica, 142:445-451 (1993) (with English Abstract).
Yoshitomi, H. et al, "Evaluation of enteric coated tablet sensitive to pancreatic lipase. I. In vitro disintegration test," Chem. Pharm. Bull., 40(7):1902-1905 (1992).
Motlekar, N. A. et al., "Zonula occludens toxin synthetic peptide derivative AT1002 enhances in vitro and in vivo intestinal absorpotion of low molecular weight heparin," Journal of Drug Targeting, 14(5):321-329 (Jun. 2006).

\* cited by examiner

Figure 1. Scatterplot of Lactulose-Mannitol ratio
Day 1 vs. Day 2

MATERIALS AND METHODS FOR THE TREATMENT OF CELIAC DISEASE

CROSS REFERENCE TO RELATED APPLICATIONS

This application is a continuation of U.S. application Ser. No. 11/955,522, filed Oct. 26, 2007 (now U.S. Pat. No. 8,034,776), which claims the benefit of United States provisional applications for patent Ser. Nos. 60/854,459, filed Oct. 26, 2006 and 60/865,236, filed Nov. 10, 2006, each of which are hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALBA_030_04US_SeqList.txt, date recorded: Aug. 12, 2011, file size 5 kilobytes).

This invention was made by or on behalf of Alba Therapeutics Corporation and the University of Maryland, Baltimore pursuant to a joint research agreement, and results from activities undertaken within the scope of the joint research agreement.

BACKGROUND OF THE INVENTION

Celiac disease (CD) is a chronic autoimmune disease that is HLA-DQ2/DQ8 haplotype restricted. Gluten, the major protein fraction of wheat, and related proteins in rye and barley are the triggering agents of the disease. Ingested gluten or its' derivative fractions (gliadin and subunits) elicit a harmful T cell-mediated immune response after crossing the small bowel epithelial barrier, undergoing deamidation by tissue transglutaminase (tTG) and engaging class II MHC molecules. While the earliest events leading to CD involves innate immune responses, evidence in the literature seems to suggest that a dysfunctional cross talk between innate and adaptive immunity is also an important pathogenic element in the autoimmune process of the disease. Under physiological circumstances, the intestinal epithelium, with its intact intercellular tight junctions (tj), serves as a key barrier to the passage of macromolecules such as gluten. When the integrity of the tj system is compromised, as in CD, a paracellular leak ("leaky gut") and an inappropriate immune response to environmental antigens (i.e., gluten) may develop. While our knowledge about tj ultrastructure and intracellular signaling events have significantly progressed during the past decade, relatively little is known about their physiological regulation secondary to extracellular stimuli and their roles in diseases such as CD.

Zonulin is an endogenous paracrine signaling protein that appears to regulate epithelial and endothelial cell tight junction function in animals and humans (Fasano, A. Ann N Y Acad Sci. 915:pp214-22 (2000); Fasano, A. Gut. 49:pp159-62 (2001); Fasano, A. et al. Lancet 355:pp1518-19 (2000); and Wang, W. et al. J Cell Sci. 113:pp4435-40 (2000)), and whose prokaryotic analogues (eg., zonula occludens toxin, or "ZOT") possess immune stimulating effects when applied to mucosal surfaces in mammals (Marinaro, M. et al. Infect Immun 67:pp1287-91 (1999); and Marinaro, M. et al. Infect Immun 71:pp1897-902 (2003). In celiac intestinal tissues and in in vitro, ex vivo, and in vivo animal experiments, gluten/gliadin cause rapid zonulin release and zonulin-dependent increases in permeability (Drago, S. et al. Scan J Gastroenterol. 41:pp408-19 (2006); Fasano, A. et al. Gastroenterol. 112:pp839-46 (1997); Ventura, A. et al. Gastroenterol. 117:pp297-303 (1999); Schuppan, D. Gastroenterol. 119:pp234-42 (2000); Norris, J. M. et al. JAMA. 293:pp2343-51 (2005); Clemente, M. G. et al. Gut. 52:pp218-23 (2003); and National Institutes of Health. Consensus Development conference Final Statement dated Aug. 9, 2004. NIH consensus Development Conference on Celiac Disease. Bethesda, Md. Jun. 28-30, 2004) in normal and diseased states. Animal models likewise have demonstrated the association of gluten, increased paracellular permeability and other autoimmune diseases, including type 1 diabetes (T1D).

AT-1001 (Larazotide Acetate) is an orally administered octapeptide (Gly Gly Val Leu Val Gln Pro Gly (SEQ ID NO:15), that appears to inhibit gliadin-induced tj disassembly by blocking putative zonulin receptors on the luminal surface of the small intestine. Pretreatment with the peptide fails to inhibit gliadin induced zonulin release, while administration of zonulin analogues or gliadin in the presence of AT-1001 fail to significantly increase intestinal permeability, confirming that the effect of the molecule is specific to the zonulin receptor (Wang, W. et al. J Cell Sci. 113:pp 4435-40 (2000); and Drago, S. et al. Scan J. Gastroenterol. 41:pp 408-19 (2006)). Experiments with ex vivo human tissue and in mice demonstrate that AT-1001 blocks zonulin binding to its putative receptor, blocks the peak of F-actin increment induced by gliadin and inhibits gliadin induced reduction in intestinal Rt (resistance) (Wang, W. et al. J Cell Sci. 113:pp 4435-40 (2000); Drago, S. et al. Scan J. Gastroenterol. 41:pp 408-19 (2006); and Clemente, M. G. et al. Gut. 52:pp 218-23 (2003)). Furthermore, intranasal pre-administration of AT-1001 in mice prevented the ZOT-induced immune response to non-self antigen challenge (Marinaro, M. et al. Infect Immun. 71:pp 1897-902 (2003)).

SUMMARY OF THE INVENTION

In some embodiments, the present invention provides compositions and methods for preventing, ameliorating and/or treating celiac disease. In one embodiment, the present invention provides a method of preventing, ameliorating and/or treating celiac disease in a subject in need thereof, comprising contacting the subject with a composition comprising an inhibitor of gliadin-induced tj disassembly. In one embodiment, the present invention provides a method of preventing, ameliorating and/or treating celiac disease in a subject in need thereof, comprising contacting the subject with a composition comprising a zonulin antagonist. In one embodiment, the inhibitor of gliadin-induced tj disassembly is a zonulin antagonist. Typically, the intestine of the subject may be contacted with the zonulin antagonist. For example, a composition comprising a zonulin antagonist may be formulated as a delayed release tablet and administered orally to a subject with celiac disease or susceptible to developing celiac disease. Suitable zonulin antagonists may be peptides and may comprise a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24. In a particular embodiment, the present invention provides a method of preventing, ameliorating and/or treating celiac disease in a subject in need thereof comprising contacting the intestine of a subject with a composition comprising a zonulin antagonist, wherein the zonulin antagonist comprises SEQ ID NO:15. Compositions for use in methods of the invention may also comprise one or more therapeutic agents. Suitable therapeutic agents include, but are not limited to, anti-inflammatories.

In some embodiments, the present invention provides methods of monitoring the treatment of celiac disease in a subject. Such methods may comprise obtaining a first sample from the subject, determining one or more of IL6, IL8, and IL10 in the first sample, obtaining a second sample, determining one or more of IL6, IL8, and IL10 in the second sample, wherein a difference in one or more of IL6, IL8, and IL10 between the first sample and the second sample is indicative of a change in severity of celiac disease in the subject. Any suitable sample may be used so long as the presence of one or more of IL6, IL8, and IL10 in the sample is related to the subject's celiac disease. For example, the samples may be Peripheral Blood Mononuclear Cells (PB-MCs) isolated form the subject and further cultured to express one or more cytokines and/or chemokines.

DETAILED DESCRIPTION OF THE INVENTION

Figure 1:
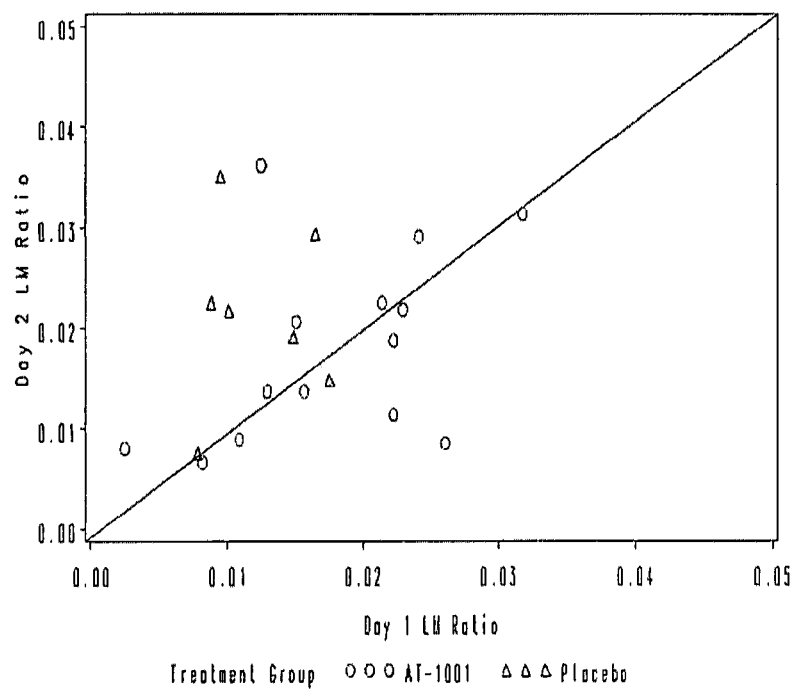
FIG. 1 is a scatterplot of Day 1 versus Day 2 L-to-M ratios in subjects enrolled in an inpatient, double-blind, randomized placebo controlled study to determine the safety, tolerability, pharmacokinetic and pharmacodynamic effects of 12 mg doses of AT-1001 in CD subjects.

As used herein a subject is any animal, e.g., mammal, upon which methods of the invention may be practiced and/or to which materials of the present invention may be administered. Subjects include, but are not limited to, humans.

As discussed above, in various embodiments, the present invention provides materials and methods for diagnosing and treating celiac disease. Further, the present invention provides materials and methods for preventing, slowing the onset of, ameliorating and/or treating celiac disease in a subject in need thereof by, inter alia, administering to a subject in need of such preventing, slowing the onset of, ameliorating and/or treating, a pharmaceutically effective amount of an antagonist of zonulin. Typically, antagonists suitable for use in the present invention bind to the zonula occludens toxin (ZOT) receptor, yet do not physiologically modulate the opening of mammalian tight junctions. In some embodiments, the antagonists of zonulin may be peptides. The term "antagonist" is defined as a compound that that prevents, inhibits, reduces or reverses the response triggered by an agonist (i.e., zonulin). In one embodiment, the present invention provides materials and methods for preventing, slowing the onset of, ameliorating and/or treating celiac disease in a subject in need thereof by, inter alia, administering to a subject in need of such preventing, slowing the onset of, ameliorating and/or treating, a pharmaceutically effective amount of an antagonist of zonulin wherein the antagonist binds to the zonula occludens toxin (ZOT) receptor, yet does not physiologically modulate the opening of mammalian tight junctions.

Antagonists of Zonulin

Any antagonist of zonulin may be used in the practice of the present invention. As used herein an antagonist of zonulin is any compound that bind to the zonulin receptor and that prevents, inhibits, reduces or reverses the response triggered by zonulin. For example, antagonists of the invention may comprise peptide antagonists of zonulin. Examples of peptide antagonists include, but are not limited to, peptides that comprise an amino acid sequence selected from the group consisting of

```
                                           (SEQ ID NO: 1)
Gly Arg Val Cys Val Gln Pro Gly, (SEQ ID NO: 2)
Gly Arg Val Cys Val Gln Asp Gly, (SEQ ID NO: 3)
Gly Arg Val Leu Val Gln Pro Gly, (SEQ ID NO: 4)
Gly Arg Val Leu Val Gln Asp Gly, (SEQ ID NO: 5)
Gly Arg Leu Cys Val Gln Pro Gly, (SEQ ID NO: 6)
Gly Arg Leu Cys Val Gln Asp Gly, (SEQ ID NO: 7)
Gly Arg Leu Leu Val Gln Pro Gly, (SEQ ID NO: 8)
Gly Arg Leu Leu Val Gln Asp Gly, (SEQ ID NO: 9)
Gly Arg Gly Cys Val Gln Pro Gly, (SEQ ID NO: 10)
Gly Arg Gly Cys Val Gln Asp Gly, (SEQ ID NO: 11)
Gly Arg Gly Leu Val Gln Pro Gly, (SEQ ID NO: 12)
Gly Arg Gly Leu Val Gln Asp Gly, (SEQ ID NO: 13)
Gly Gly Val Cys Val Gln Pro Gly, (SEQ ID NO: 14)
Gly Gly Val Cys Val Gln Asp Gly, (SEQ ID NO: 15)
Gly Gly Val Leu Val Gln Pro Gly, (SEQ ID NO: 16)
Gly Gly Val Leu Val Gln Asp Gly, (SEQ ID NO: 17)
Gly Gly Leu Cys Val Gln Pro Gly, (SEQ ID NO: 18)
Gly Gly Leu Cys Val Gln Asp Gly, (SEQ ID NO: 19)
Gly Gly Leu Leu Val Gln Pro Gly, (SEQ ID NO: 20)
Gly Gly Leu Leu Val Gln Asp Gly, (SEQ ID NO: 21)
Gly Gly Gly Cys Val Gln Pro Gly, (SEQ ID NO: 22)
Gly Gly Gly Cys Val Gln Asp Gly, (SEQ ID NO: 23)
Gly Gly Gly Leu Val Gln Pro Gly,
and
                                          (SEQ ID NO: 24)
Gly Gly Gly Leu Val Gln Asp Gly
```

When the antagonist is a peptide, any length of peptide may be used. Generally, the size of the peptide antagonist will range from about 6 to about 100, from about 6 to about 90, from about 6 to about 80, from about 6 to about 70, from about 6 to about 60, from about 6 to about 50, from about 6 to about 40, from about 6 to about 30, from about 6 to about 25, from about 6 to about 20, from about 6 to about 15, from about 6 to about 14, from about 6 to about 13, from about 6 to about 12, from about 6 to about 11, from about 6 to about 10, from about 6 to about 9, or from about 6 to about 8 amino acids in length. Peptide antagonists of the invention may be from about 8 to about 100, from about 8 to about 90, from about 8 to about 80, from about 8 to about 70, from about 8 to about 60, from about 8 to about 50, from about 8 to about 40, from about 8 to about 30, from about 8 to about 25, from about 8 to about 20, from about 8 to about 15, from about 8 to about 14, from about 8 to about 13, from about 8 to about 12, from about 8 to about 11, or from about 8 to about 10 amino acids in length. Peptide antagonists of the invention may be from about 10 to about 100, from about 10 to about 90, from about 10 to about 80, from about 10 to about 70, from about 10 to about 60, from about 10 to about 50, from about 10 to about 40, from about 10 to about 30, from about 10 to about 25, from about 10 to about 20, from about 10 to about 15, from about 10 to about 14, from about 10 to about 13, or from about 10 to about 12 amino acids in length. Peptide antagonists of the invention may be from about 12 to about 100, from about 12 to about 90, from about 12 to about 80, from about 12 to about 70, from about 12 to about 60, from about 12 to about 50, from about 12 to about 40, from about 12 to about 30, from about 12 to about 25, from about 12 to about 20, from about 12 to about 15, or from about 12 to about 14 amino acids in length. Peptide antagonists of the invention may be from about 15 to about 100, from about 15 to about 90, from about 15 to about 80, from about 15 to about 70, from about 15 to about 60, from about 15 to about 50, from about 15 to about 40, from about 15 to about 30, from about 15 to about 25, from about 15 to about 20, from about 19 to about 15, from about 15 to about 18, or from about 17 to about 15 amino acids in length.

The peptide antagonists can be chemically synthesized and purified using well-known techniques, such as described in High Performance Liquid Chromatography of Peptides and Proteins: Separation Analysis and Conformation, Eds. Mant et al., C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

Compositions Comprising One or More Zonulin Antagonists

In on embodiment, compositions of the invention may comprise one or more zonulin antagonists. An example of suitable antagonists of zonulin are peptide GGVLVQPG (SEQ ID NO: 15) and derivatives thereof, particularly derivatives having one or more conservative amino acid substitutions. Such compositions may be used to treat celiac disease.

Typically, compositions of the invention will comprise a pharmaceutically effective amount of the antagonist. The pharmaceutically effective amount of an antagonist of zonulin will vary depending upon the severity of the celiac disease being treated, as well as the age, weight and sex of the subject being treated. Generally, the amount of antagonist used for preventing, ameliorating and/or treating celiac disease, e.g., to inhibit zonulin biological activity, is in the range of about 1.0 μg to 1 g, preferably about 1 mg to about 1000 mg, or from about 10 mg to about 100 mg, or from about 10 mg to about 50 mg, or from about 10 mg to about 25 mg of antagonist.

EXAMPLES

Example 1

This was an inpatient, double-blind, randomized placebo controlled study to determine the safety, tolerability, pharmacokinetic and pharmacodynamic effects of 12 mg doses of AT-1001 in CD subjects. One cohort of 24 subjects was planned, with a 2:1 randomization (drug:placebo) for once daily dosing on Days 1, 2 and 3. On Day 2, all subjects would receive a 2.5 gram oral gluten challenge in single blind fashion.

Efficacy endpoints included changes in urinary lactulose-to-mannitol (L-to-M) ratios assessed on study days 1, 2, 3, and 7, self-reported measures of GI discomfort (visual analogue pain scale and three ordinal questions about bowel function), GI adverse events (AEs) an ordinal global outcomes assessment, urinary nitrites/nitrates and PBMC cell markers and cytokine levels.

Pharmacokinetic measures included serial plasma levels of AT-1001 collected at various times following administration of each treatment. Safety measures included monitoring of AEs, standard clinical panels for chemistry, hematology, and urinalysis, pregnancy screening, EKG, vital signs and physical exam findings.

Subjects:

Twenty one (21) male and female volunteers between 18 and 59 years of age, diagnosed with CD by biopsy and positive antibody screen, on gluten-free diets for at least 6 months prior to enrollment, and presenting with Anti-Tissue Transglutaminase (tTG) titres≤10 EU were enrolled. Subjects taking medications such as proton pump inhibitors, NSAIDs, immune suppressants, pancreatic enzyme replacement, oral corticosteroids, fibrates and amphetamines (eg., ADHD meds) were excluded, as were active smokers and subjects with recent alcohol or drug use, recent GI disturbances and positive HIV, Hepatitis B or Hepatitis C tests.

Conduct of the Study

After informed consent, subjects were randomized to receive AT-1001 capsules containing enteric coated, multiparticulate beads with a dose of 12 mg or matching placebo once daily for three consecutive days. On the morning of Day 1 all subjects were admitted to the Clinical Research Unit for re-confirmation of eligibility criteria and safety assessments. That afternoon fasting subjects were administered AT-1001 or matching placebo, followed by a blinded sham gluten challenge ½ hour later. One-half hour after sham challenge, a solution of sucrose, lactulose and mannitol was administered for initial intestinal permeability measures, followed by an 8-hour urine collection. On the afternoon of Day 2, subjects were again administered drug or placebo, and 0.5 hour later were administered gluten in blinded fashion, followed by the intestinal permeability measure. On Day 3 subjects were again administered drug or placebo, followed by a blinded sham gluten challenge and intestinal permeability assay, and then discharged. Blood samples were drawn each treatment day for safety, pharmacokinetic, pharmacodynamic and immunologic evaluations. Patients returned on Day 7 for additional follow-up assessments.

Patient Assessment:

At bedtime on Days 1 and 2 and at clinic discharge on Day 3, subjects recorded their level of GI discomfort by marking an "X" on a 10 cm linear line. GI daily symptoms were also assessed by answering three questions ordinal related to bowel function. At study termination, subjects were administered a global assessment tool, asked to choose one of seven ordinal levels in response to a question related to any change in their disease status since study enrollment.

Safety Assessments:

All clinical events, including either observed or volunteered problems, complaints or symptoms were recorded regardless of whether the clinical event was associated with study treatment. Spontaneous adverse events collected throughout the study were categorized according to WHO adverse reaction terminology and evaluated for duration, intensity, and possible association with the study drug per ICH guidelines. In addition, the following procedures were performed at various points throughout the course of the study: vital signs, complete physical exams, 12-lead electrocardiograms, full clinical (safety) laboratory analyses, serum pregnancy, urine drug screen and HIV and hepatitis serologies.

Intestinal Permeability Assay:

For the assessment of intestinal permeability, a permeability probe solution containing 100 gm sucrose, 7.5 gm lactulose and 2 gm mannitol in 450 ml was administered orally. Probe solution was administered 1 hour after drug/placebo dosing and ½ hr after gluten/sham challenge on Days 1, 2, and 3 and again during follow-up visits on Day 7. Subject urines were thereafter collected for 8 hours following ingestion of the solution and frozen and stored for analysis of sucrose, lactulose and mannitol recoveries via standardized methodologies (Doig, C. J. et al. Am J Respir Crit Care Med. 158(2): pp444-51 (1998)).

Dietary Restrictions

Throughout the course of the study, subjects remained on a strict gluten free diet. With the exception of the dietary gluten/sham challenge, subjects fasted for 3 hours (NPO, except water) prior to and 4.5 hours after the administration of drug/placebo on Days 1, 2 and 3. At 4.5 hours, subjects were allowed to resume a diet limited by the avoidance of foods/liquids containing added sugars and artificial sweeteners. Upon completion of the 8-hour urine collection subjects resumed their normal gluten free diet.

Dietary Gluten Challenge

A snack, consisting of 4 oz of gluten-free pudding was provided to all subjects 0.5 hours after drug/placebo administration on Days 1, 2 and 3. On Day 2, amygluten 160 powder, 2.5 gm (Tate and Lyle of Decatur, Ill.) was stirred into the pudding by clinic kitchen staff immediately prior to serving, and served to all subjects in single blind fashion.

Pharmacokinetic Evaluation:

Plasma samples were taken at 0, 2, and 3 hours following administration of each treatment to determine whether quantifiable AT-1001 concentrations were present in plasma following single oral doses and to characterize pharmacokinetic behavior. AT-1001 levels were determined using a validated HPLC MS-MS method with a lower limit of quantification of 0.5 ng/ml.

Other Pharmacodynamic Evaluations:

Zonulin Levels were determined using published techniques (see Fasano et al. US patent publication 20060128626 A1).

Peripheral Blood Mononuclear Cells ("PBMCs"):

The phenotype and function of antigen presenting cells, including dendritic cells, monocytes and T cells were evaluated by means of studying a panel of activation, maturation and homing markers expressed on the surface of immune cells under varying conditions. On Days 2, 3 and 7, blood was drawn, processed and frozen. After thawing, PBMCs were isolated and cultured for 24 hours under standard conditions. Supernatant cytokine production, surface expression of maturation and activation markers were determined utilizing luminex ELISA and flow cytometry. IL-6, IL-8, tumor necrosis factor (TNF)-α, interferon (IFN)-α, and IP-10 were measured and surface markers CD40, CD80, CD86, HLA-DR; CD4, CD25, CD28, CD4OL, and CXCR3 were measured using conventional techniques.

Urine Nitrate/Nitrite Levels

On Days 2 and 3 a baseline spot urine sample was collected for nitrite/nitrate determinations as a surrogate for inducible nitric oxide synthetase (iNOS) activity.

Statistical Analysis:

This single center, randomized, placebo controlled study was not designed to have adequate statistical power for hypothesis testing. Treatment assignment was randomized at a ratio of 2:1 drug to placebo; subjects were considered protocol valid if they receive study medication and completed all study evaluations without noteworthy study protocol violations. All continuous data, as well as differences between baseline and endpoint values (where applicable), were analysed descriptively, including number of observations (n), median, mean, standard deviation (SD), minimum, and maximum. Frequencies and percentages were used for summarizing discrete (categorical) variables. Changes were assessed as the difference between the baseline value and the observed post-dose value unless otherwise stated.

All adverse events reported during the study were listed, documenting course, severity, and outcome and summarized by treatment, giving the number of subjects who experienced an adverse event, the maximum severity, and body system. GI adeverse events for each arm were tabulated by subject count and compared via Fisher's exact test.

Clinical laboratory parameters, vital signs, and physical exam results were summarized with the statistics of n, mean, standard deviation, median and range or frequencies and percentages, as appropriate. EKG results were classified as normal and abnormal. PR, RR, QRS, QT, and QTc intervals will be carefully examined and abnormalities tabulated.

Lactulose:mannitol (recovered) ratios were used to quantify small bowel paracellular permeabilities for each collection, and geometric means and geometric mean fold-ratios were calculated for every observation. Comparisons were made by summary of observed L-M ratios by day and study group, summary of Day 1-to-Day X comparisons by study group and summary of study groups comparison; 2 sided t-tests were utilized for comparative analyses.

For PBMC cell markers, geometric means and geometric mean fold-ratios were calculated; within and between group t-test p-values for log (later hour/hour 3 ratio) were determined. For PBMC supernatant cytokines, geometric means and mean fold-ratios were of observed values were calculated; within and between group t-test p-values for log (later hour/hour 0) were determined.

For patient global assessment, seven ordinal levels were collected once at the end of the study, displayed as proportions, and analyzed by exact CMH test in StatXact software. For GI discomfort, a 10 centimeter visual analogue scale was collected each night, displayed as means±std. dev., and analyzed by a linear, mixed effect model identical to the model for the primary outcome. GI symptoms collected nightly were displayed by proportions and mean±std. dev., and analyzed by GEE model in SAS/STAT PROC GENMOD with terms for treatment group, Day, their interaction, age, and gender.

Results

Subjects:

Twenty four patients with CD were planned for enrollment according to the inclusion/exclusion criteria of the study. Subjects had a screening visit up to eight weeks prior to the first dose to ensure suitability for study participation. A total of 66 subjects underwent screening visits and of these, 21 subjects were randomized and enrolled in the study. The remaining 45 subjects were excluded for failure to meet exclusion or inclusion criteria or failure to consent. All 21 enrolled subjects received study medication (7 placebo, 14 AT-1001) and completed the study. Demographic characteristics are listed on Table 1.

TABLE 1

| N | | Placebo 7 | AT-1001 14 | Combined 21 |
|---|---|---|---|---|
| AGE (YEARS) | Mean | 33.3 | 37.6 | 36.2 |
| | SD | 9.9 | 8.1 | 8.8 |
| | Range | 21-50 | 27-52 | 21-52 |
| HEIGHT (CM) | Mean | 168.6 | 167.3 | 167.7 |
| | SD | 7.2 | 7.6 | 7.3 |
| | Range | 161-182 | 157-184 | 157-184 |
| Weight (kg) | Mean | 71.26 | 61.90 | 65.02 |
| | SD | 12.62 | 11.96 | 12.70 |
| | Range | 59.4-94.2 | 49.6-82.8 | 49.6-94.2 |
| BMI (kg/m$^2$) | Mean | 25.00 | 22.01 | 23.00 |
| | SD | 3.51 | 3.27 | 3.57 |
| | Range | 21.7-29.5 | 18.5-29.3 | 18.5-29.5 |
| GENDER [Number] (%) | Female | 5 (71.4) | 12 (85.7) | 17 (81.0) |
| | Male | 2 (28.6) | 2 (14.3) | 4 (19.0) |
| ANTI-TTG TITRE [I.U.] | Mean | | | |
| | SD | | | |
| | Range | | | |

Adverse Events and Safety Data:

Safety

There were no deaths, SAEs, significant AEs, or withdrawals due to AEs reported during this study. There were no clinically significant abnormalities in safety laboratory tests, vital signs, ECG intervals, ECG morphology, or physical examinations during this study. Forty-nine AEs were mild in intensity, three AEs were moderate in intensity, and there were no severe AEs. All AEs resolved before the end of the study. Summary details for the non-serious, treatment-emergent adverse events (AEs) reported during this study are summarized in Table 2:

TABLE 2

|  | Placebo (N = 7) | AT-1001 (N = 14) | Overall (N = 21) |
|---|---|---|---|
| Number (%) of subjects reporting an AE | 7 (100) | 10 (71) | 17 (81) |
| Number (%) of subjects discontinued study due to AE | 0 (0) | 0 (0) | 0 (0) |
| Total number of AEs reported | 20 | 32 | 52 |
| Number (%) of related* AEs | 1 (5) | 1 (3) | 2 (4) |
| Number (%) of serious AEs | 0 (0) | 0 (0) | 0 (0) |

*Related = Possible, probably, definite combined causalities

The most commonly reported AE was diarrhea and the majority of AEs were gastrointestinal. Importantly, the comparison of gastrointestinal adverse events in general, and diarrhea in specific, between drug and placebo group (Table 3) reveals a statistically significant reduction in symptoms in the group receiving AT-1001 throughout the course of the study, suggesting a protective effect for the drug. Specifically, every CD-related symptom (see table 3) except vomiting was more frequently experienced by patients assigned to the placebo group compared to those belonging to the AT-1001 group, with diarrhea achieving statistical significance.

TABLE 3

Summary of Gastrointestinal Adverse Events

|  | Subject Count (%) By Treatment | | P-Value |
|---|---|---|---|
|  | Placebo (N = 7) | AT-1001 (N = 14) | (Fisher's exact test.) |
| Gastrointestinal Disorders* CD-RELATED | 7 (100%) | 6 (43%) | 0.018 |
| Abdominal Discomfort | 2 (29%) | 0 (0%) | 0.10 |
| Constipation | 1 (14%) | 0 (0%) | 0.33 |
| Diarrhoea* | 5 (71%) | 2 (14%) | 0.017 |
| Flatulence | 2 (29%) | 2 (14%) | 0.57 |
| Vomiting | 1 (14%) | 3 (21%) | 1 |
| NOT CD-RELATED |  |  |  |
| Eructation | 0 (0%) | 1 (7%) | 1 |
| Gastrooesophageal Reflux | 1 (14%) | 1 (7%) | 1 |
| Nausea | 2 (29%) | 4 (29%) | 1 |
| Stomach Discomfort | 0 (0%) | 2 (14%) | 0.53 |
| Dyspepsia | 0 (0%) | 3 (21%) | 0.52 |

*p < 0.05

Pharmacokinetics:

All plasma concentrations were below the limit of quantification (<0.05 ng/ml).

Serum Zonulin.

Serum zonulin levels increased on Day 2 following exposure to gluten, irrespective of the group assignment (placebo vs AT-1001). These results confirm our previous report demonstrating that AT-1001 inhibitory effect on intestinal permeability is related to its capability to prevent zonulin binding to its putative receptor, rather than affecting gluten-induced zonulin release.

Intestinal Permeability:

For the primary outcome, the Day 2-to-Day 1 change in urinary Lactulose-to-Mannitol (L-to-M) ratio, there was a significant increase in the placebo group (p-value 0.041) and no increase in the AT-1001 group. This trend remained throughout the course of the study. The between-group comparison of the Day 1 to Day 2 changes, the placebo to AT-1001 GM "ratio of ratios", was 1.65, representing an increase of 65% in permeability in the placebo vs. test groups that nearly approached statistical significance (p-value 0.074 for a two-sided test of no treatment effect), and remained elevated throughout the course of the study, confirming the effects of gluten exposure on intestinal permeability and the protective effects of AT-1001. The secondary analyses were qualitatively similar but weaker.

Table 4 displays the three levels of comparison of results for the Day 2 to Day 1, Day 3 to Day 1 and Day 7 to Day 1 changes in L-M ratios, 1. P-value for a paired t-test, based on $\log_{10}$ (L-M-RATIO) of no within-group change 2. P-value for a t-test of no between-group difference in the Hour 0-to-Later Hour ratio.

Figure 2:
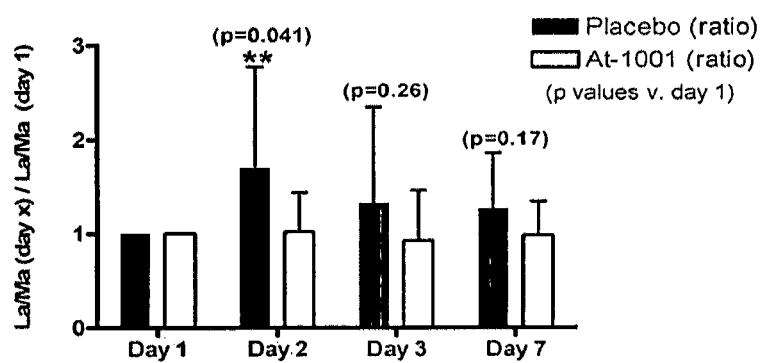
FIG. 2 is a bar graph showing the L to M ratios on the various days as measured in subjects enrolled in an inpatient, double-blind, randomized placebo controlled study to determine the safety, tolerability, pharmacokinetic and pharmacodynamic effects of 12 mg doses of AT-1001 in CD subjects.
Figure 3:
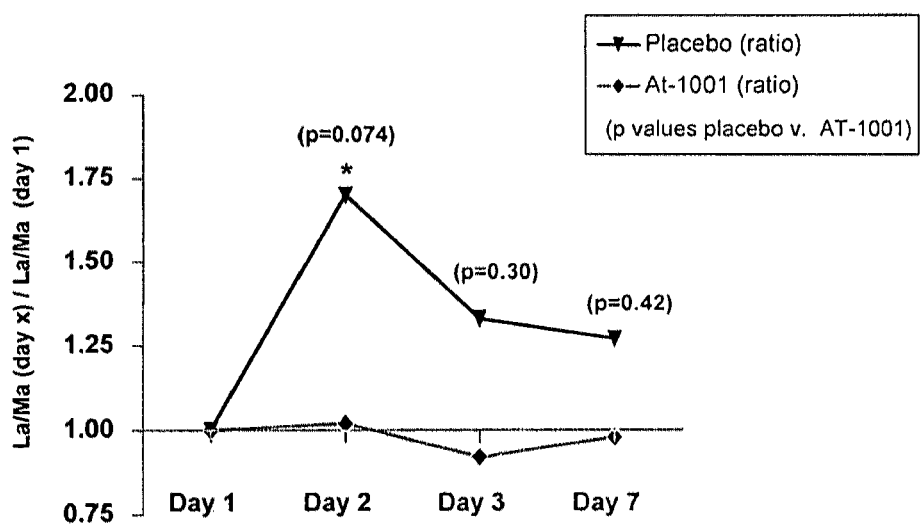
FIG. 3 is a line graph of the L to M ratios from FIG. 2. Placebo n=7; AT-1001 n=14. Intestinal barrier function during a supramaximal stimulus (2.5 gm gluten challenge) is maintained by 12 mg AT-1001. Suggests AT-1001 blocks persistent leak and immune activation. fe; no SAE's. Statistical significance between placebo & drug treated group for GI adverse events. P-value for a t-test of no within group difference Hour 0-to-Later Hour ratio Placebo Day 1-Day 2 change p=0.04.

FIG. 1 is a scatterplot of Day 1 versus Day 2 L-to-M ratios. Data points with ratios>1 correspond to subjects with a greater L-to-M ratio after the gluten challenge than before it; these data points are located above the 45° line while points below the 45° line display L-to-M ratios that are less on Day 2 than on Day 1. A greater percentage of subjects in the AT-1001 group fell below the 45° line, while 5 (71.4%) of placebo subjects had Day 1-to-Day 2 ratios>1 and 2 (28.6%) subjects had ratios≤1. Among the 14 subjects receiving AT-1001, 6 (42.9%) had ratios>1 and 8 (57.1) had ratios≤1. FIG. 2 is a bar graph showing the L to M ratios on the various days. FIG. 3 is a line graph of the L to M ratios.

TABLE 4

Summary of L-to-M ratios Findings

| L-M-RATIO by Day and Treatment |  | Day 1 | Day 2 | Day 3 | Day 7 |
|---|---|---|---|---|---|
| Observed Values | Placebo (N = 7) | GM = 0.012 CI: 0.009-0.016 | GM = 0.020 CI: 0.012-0.031 | GM = 0.015 CI: 0.008-0.029 | GM = 0.015 CI: 0.009-0.023 |
|  | AT-1001 (N = 14) | GM = 0.015 CI: 0.011-0.022 | GM = 0.016 CI: 0.011-0.022 | GM = 0.014 CI: 0.010-0.021 | GM = 0.015 CI: 0.011-0.021 |
| Ratios Compared to Day 1 by Group[1] | Placebo (N = 7) |  | GM = 1.70 CI: 1.03-2.77 p = 0.041 | GM = 1.33 CI: 0.76-2.35 p = 0.26 | GM = 1.27 CI: 0.87-1.86 p = 0.17 |
|  | AT-1001 (N = 14) |  | GM = 1.02 CI: 0.73-1.44 p = 0.88 | GM = 0.92 CI: 0.58-1.46 p = 0.71 | GM = 0.98 CI: 0.62-1.54 p = 0.92 |
| Pleacebo at AT-1001 summary[2] |  |  | GM = 1.65 CI: 0.95-2.87 p = 0.074 | GM = 1.45 CI: 0.71-2.97 p = 0.30 | GM = 1.30 CI: 0.67-2.54 p = 0.42 |

Fractional excretion of lactulose and mannitol were secondary outcomes of the study. Using the same methods as for the primary L-to-M ratio outcome, Day 1 vs. Day 2, Day 1 vs. Day 3 and Day 1 vs. Day 7 analyses were performed for each of the two outcomes. Throughout the course of the study, there was a decrease in fractional excretion of lactulose in the AT-1001 group that achieved its nadir on Day 3 (27%; p=0.079) but never reached significance. From Day 1 to 2 a 24% increase in the fractional excretion of lactulose was observed among placebo recipients as shown in Table 5, and a 36% greater difference in response between placebo and AT-1001 was observed through Day 3. The comparison of Days 1 and 7, five days after gluten challenge and four days after last drug dosing, shows a 7% decrease in the placebo group and a 12% decrease in the AT-1001 group, for a 1.06 ratio between groups. That was not significant.

TABLE 5

Summary of Fractional Excretion of Lactulose Findings

| Fractional Lactulose by Day and Treatment | | Day 1 | Day 2 | Day 3 | Day 7 |
|---|---|---|---|---|---|
| Observed Values | Placebo (N = 7) | GM = 0.0026 CI: 0.0016-0.0043 | GM = 0.0033 CI: 0.0024-0.0044 | GM = 0.0026 CI: 0.0017-0.0040 | GM = 0.0025 CI: 0.0017-0.0035 |
| | AT-1001 (N = 14) | GM = 0.0031 CI: 0.0022-0.0043 | GM = 0.0028 CI: 0.0020-0.0039 | GM = 0.0022 CI: 0.0016-0.0032 | GM = 0.0027 CI: 0.0021-0.0035 |
| Ratios Compared to Day 1 by Group[1] | Placebo (N = 7) | | GM = 1.24 CI: 0.68-2.26 p = 0.41 | GM = 0.99 CI: 0.58-1.72 p = 0.98 | GM = 0.93 CI: 0.46-1.89 P = 0.82 |
| | AT-1001 (N = 14) | | GM = 0.91 CI: 0.63-1.32 p = 0.61 | GM = 0.73 CI: 0.51-1.04 p = 0.079 | GM = 0.88 CI: 0.59-1.33 P = 0.52 |
| Placebo to AT-1001 summary[2] | | | GM = 1.36 CI: 0.73-2.53 p = 0.32 | GM = 1.36 CI: 0.76-2.45 p = 0.29 | GM = 1.06 CI: 0.53-2.13 P = 0.87 |

[1] P-value for a paired t-test, based on $\log_{10}$(Fractional Lactulose) of no within-group change.
[2] P-value for a t-test of no between-group difference in the Hour 0-to-Later Hour ratio.

The fractional excretion of mannitol comparing Day 1 and subsequent days is shown in Table 6 and demonstrates a reduced mannitol excretion in the placebo group throughout the study that achieved statistical significance on Day 3 (25%; p=0.026). The group receiving AT-1001 demonstrated a trend to reduced fractional mannitol excretion but was not significant. The between-group comparisons were not significant.

Immune Markers:
Nitrate/Nitrite

Nitrite values were not detected in either the placebo or AT-1001 groups. The placebo group experienced a significant increase in urine nitrates Day 2 baseline vs. Day 1 baseline, suggesting a possible induction of iNOS in the placebo group that was absent in the AT-1001 group.

TABLE 6

Summary of Urine Nitrate Findings[i]

| | | Nitrate by Day and Treatment | |
|---|---|---|---|
| | | Day 2 Pre-Dose | Day 3 Pre-Dose |
| Observed Values | Placebo (N = 7) | GM = 90.67 CI: 50.32-163.37 | GM = 161.46 CI: 106.87-243.93 |
| | AT-1001 (N = 14) | GM = 94.84 CI: 63.42-141.83 | GM = 128.23 CI: 89.81-183.10 |

TABLE 6

Summary of Fractional Excretion of Mannitol Findings

| Fractional Mannitol by Day and Treatment | | Day 1 | Day 2 | Day 3 | Day 7 |
|---|---|---|---|---|---|
| Observed Values | Placebo (N = 7) | GM = 0.23 CI: 0.15-0.35 | GM = 0.17 CI: 0.12-0.23 | GM = 0.17 CI: 0.12-0.24 | GM = 0.17 CI: 0.13-0.21 |
| | AT-1001 (N = 14) | GM = 0.20 CI: 0.13-0.30 | GM = 0.18 CI: 0.14-0.22 | GM = 0.16 CI: 0.13-0.20 | GM = 0.18 CI: 0.15-0.21 |
| Ratios Compared to Day 1 by Group[1] | Placebo (N = 7) | | GM = 0.74 CI: 0.51-1.05 p = 0.079 | GM = 0.75 CI: 0.59-0.95 p = 0.026* | GM = 0.73 CI: 0.46-1.17 p = 0.15 |
| | AT-1001 (N = 14) | | GM = 0.89 CI: 0.64-1.25 p = 0.48 | GM = 0.79 CI: 0.53-1.19 p = 0.24 | GM = 0.90 CI: 0.62-1.32 p = 0.57 |
| Placebo to AT-1001 summary[2] | | | GM = 0.82 CI: 0.49-1.38 p = 0.44 | GM = 0.94 CI: 0.53-1.68 p = 0.83 | GM = 0.81 CI: 0.45-1.48 p = 0.48 |

[1] P-value for a paired t-test, based on $\log_{10}$(Frac Mannitol) of no within-group change.
[2] P-value for a t-test of no between-group difference in the Hour 0-to-Later Hour ratio.

TABLE 6-continued

Summary of Urine Nitrate Findings¡

| | | Nitrate by Day and Treatment | |
|---|---|---|---|
| | | Day 2 Pre-Dose | Day 3 Pre-Dose |
| Within-group Comparisons | Placebo (N = 27) | | GM = 1.78 CI: 1.13-2.81 p = 0.021[1],* |
| | AT-1001 (N = 14) | | GM = 1.43 CI: 0.95-2.14 p = 0.083[1] |
| Placebo to AT-1001 summary | | | GM = 0.80 CI: 0.46-1.38 p = 0.40[2] |

[1]P-value for a paired t-test, based on $\log_{10}$(Nitrate) of no within-group change comparing Day 3/Pre-Dose to Day 2/Pre-Dose.
[2]P-value for a t-test of no between-group difference.

Pro-Inflammatory Cytokines and Chemokines

Figure 4:
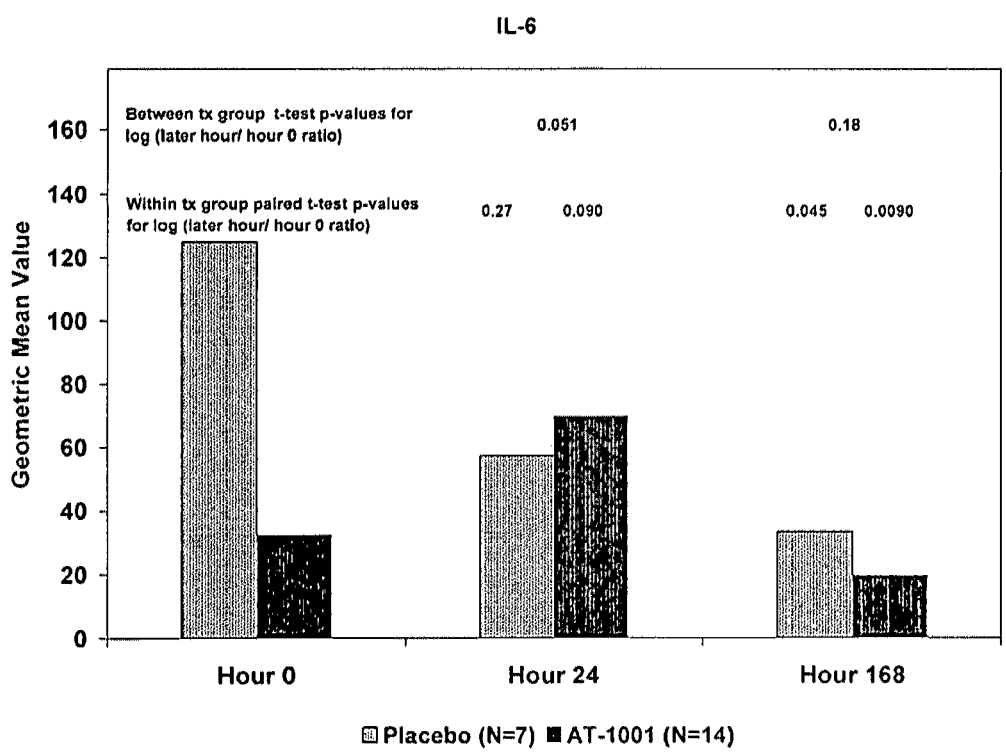
FIG. 4 is a bar graph showing IL6 concentration in placebo versus treatment on at hours 0, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.

As shown in FIG. 4, the concentrations of Interleukin-6 (IL-6) within the AT-1001 group decreased significantly from Day 2, 0 hour to Day 7 ($p<0.01$). IL-6 levels also decreased from Day 2, 0 hour to Day 7 in the placebo group ($p<0.05$). On Day 2, 0 hour and Day 7, IL-6 levels were similar between the AT-1001 and placebo groups.

Figure 5:
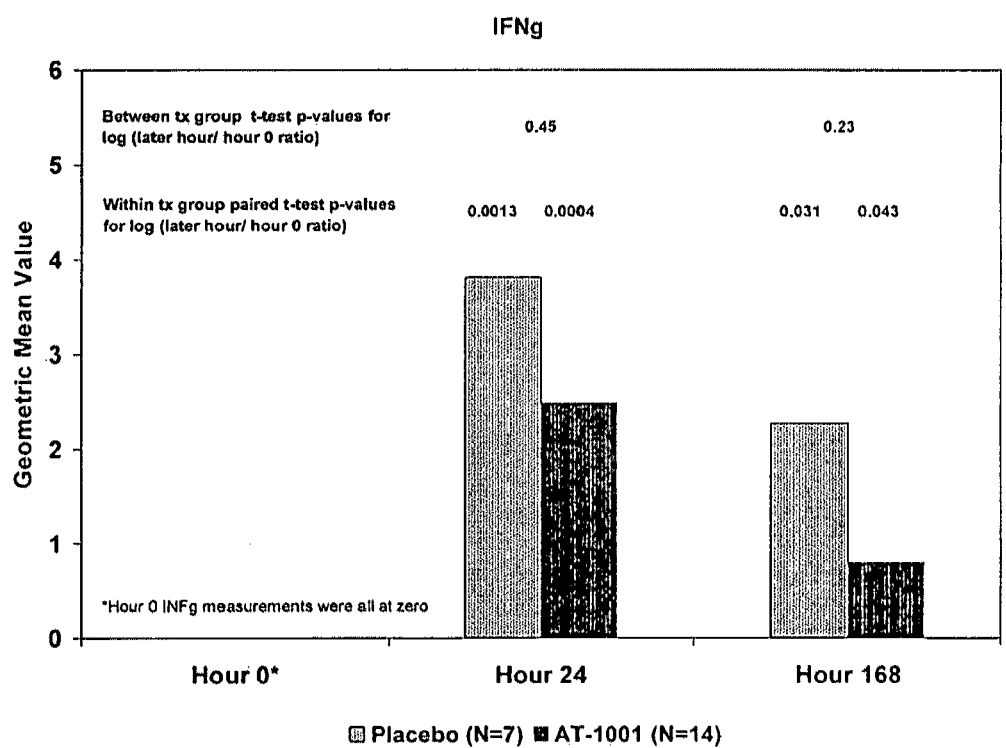
FIG. 5 is a bar graph showing IFN-γ concentration in placebo versus treatment on at hours 0, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.

Tumor necrosis factor-$\alpha$ (TNF-$\alpha$) levels did not change significantly in either group during the study and were not significantly different on Day 7. Interferon-$\gamma$ was not detectable on Day 2, 0 hour. IFN-$\gamma$ levels increased during the study in both dose groups (FIG. 5). Interleukin-15 (IL-15) was below the detection level of the assay for both groups throughout the study.

Chemokines

Figure 6:
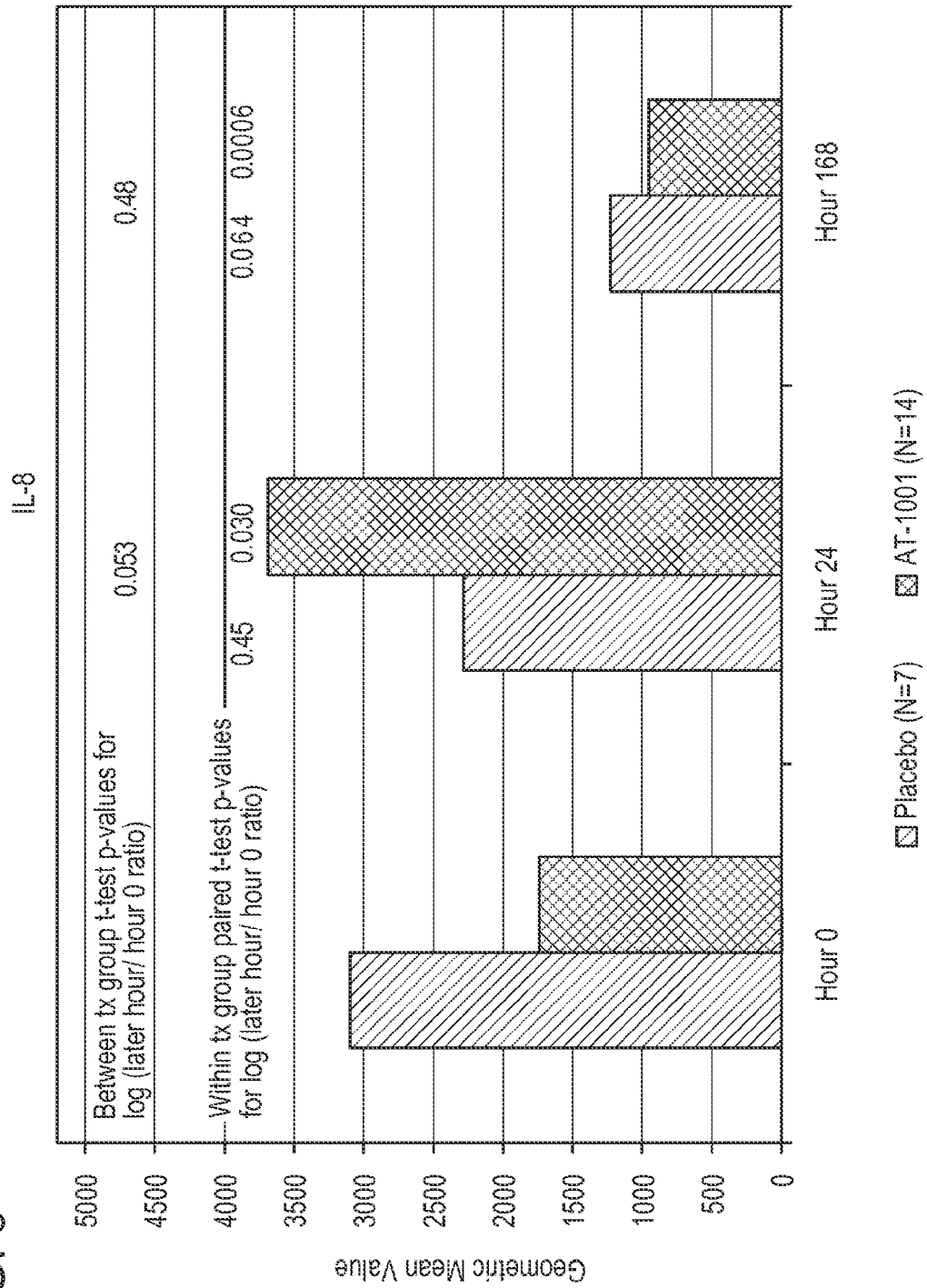
FIG. 6 is a bar graph showing IL8 concentration in placebo versus treatment on at hours 0, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.

There were no significant differences in interleukin-8 (IL-8) levels between the AT-1001 and placebo groups Day 2, 0 hour and Day 7 (FIG. 6). IL-8 concentrations decreased significantly within the AT-1001 group from Day 2, 0 hour to Day 3, 0 hour ($p<0.05$) and to Day 7 ($p<0.001$). There were no significant differences in Inducible Protein-10 (IP-10) between the AT-1001 and placebo groups between Day 2, 0 hour and Day 7.

Anti-Inflammatory Cytokines

Figure 7:
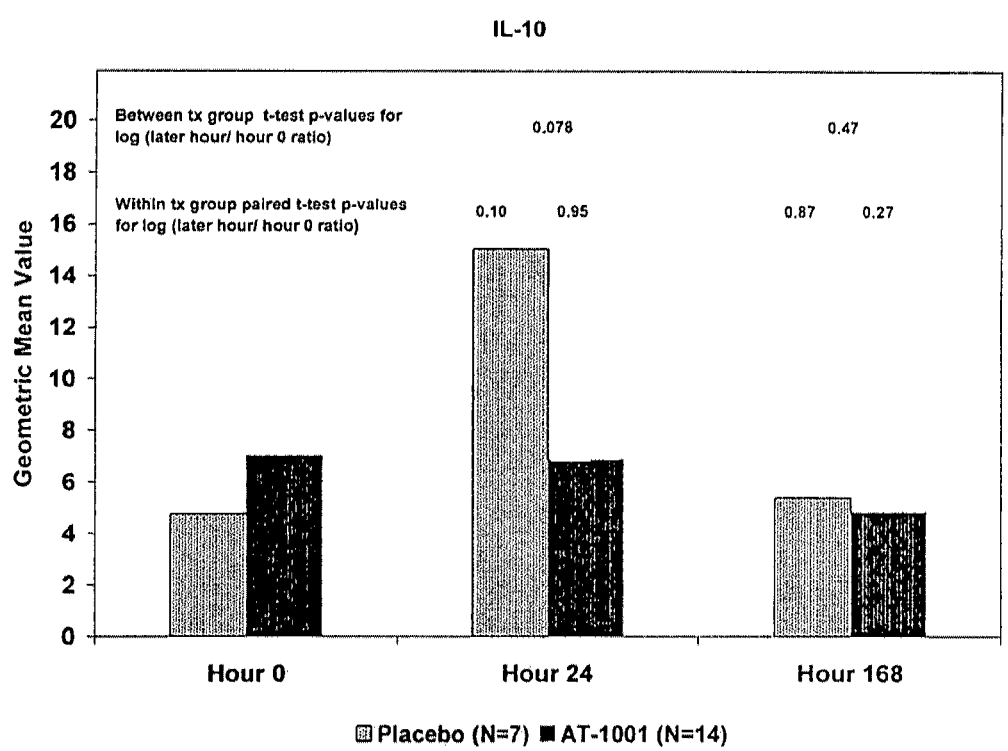
FIG. 7 is a bar graph showing IL10 concentration in placebo versus treatment on at hours 0, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.

Interleukin-13 (IL-13) levels were below detection limit of the assay for both groups throughout the study. Interleukin-10 (IL-10) levels appeared to increase in the placebo group from Day 2, 0 hour to Day 3, 0 hour; this increase approached statistical significance (p=) while they remained unchanged in the AT-1001 dose group (FIG. 7). The difference in IL-10 between AT-1001 and placebo groups approached statistical significance on Day 2, 0 hour (p=).

Activation Markers

Figure 8:
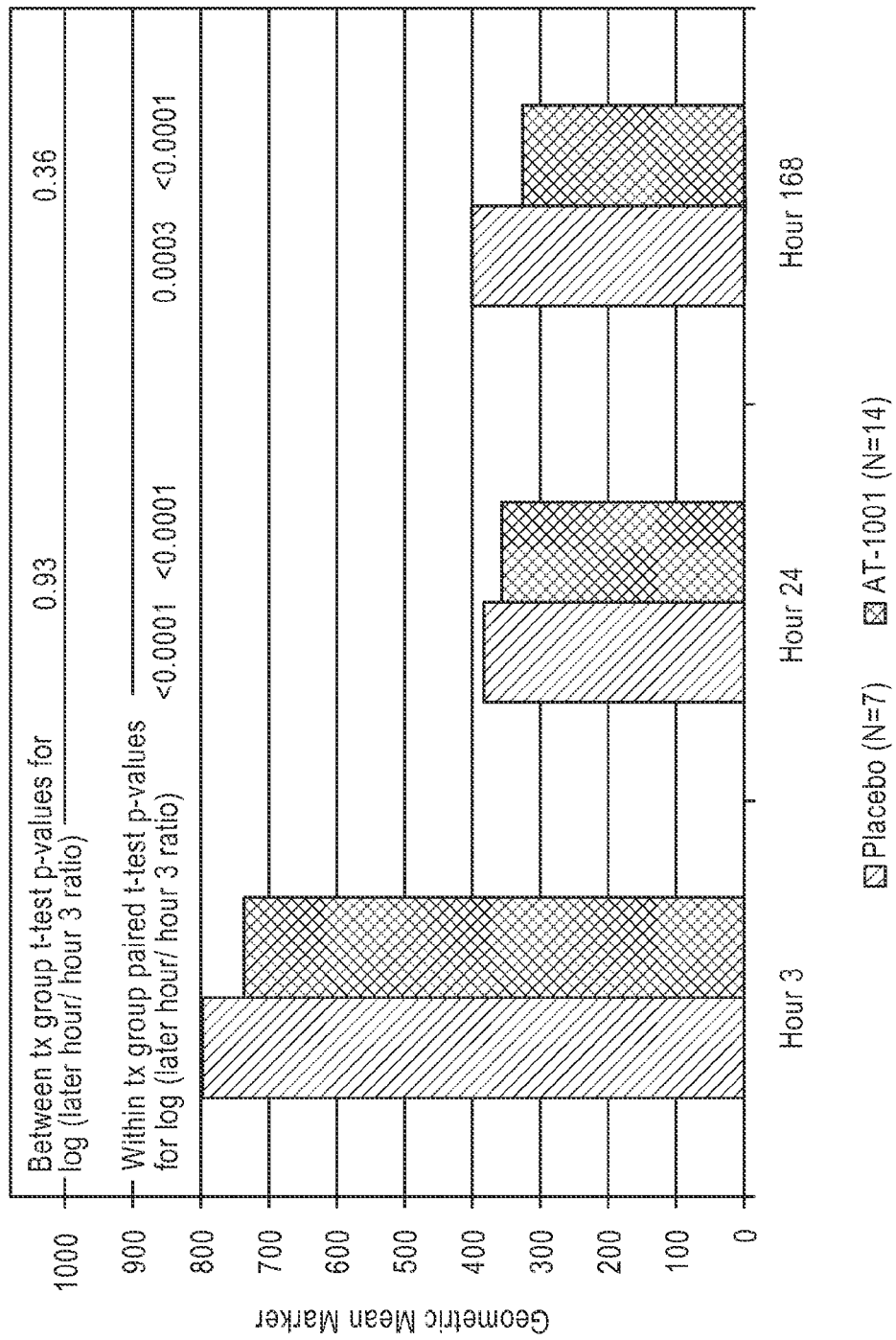
FIG. 8 is a bar graph showing Mean Fluorescence Intensity of activation markers in placebo versus treatment on at hours 3, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.
Figure 9:
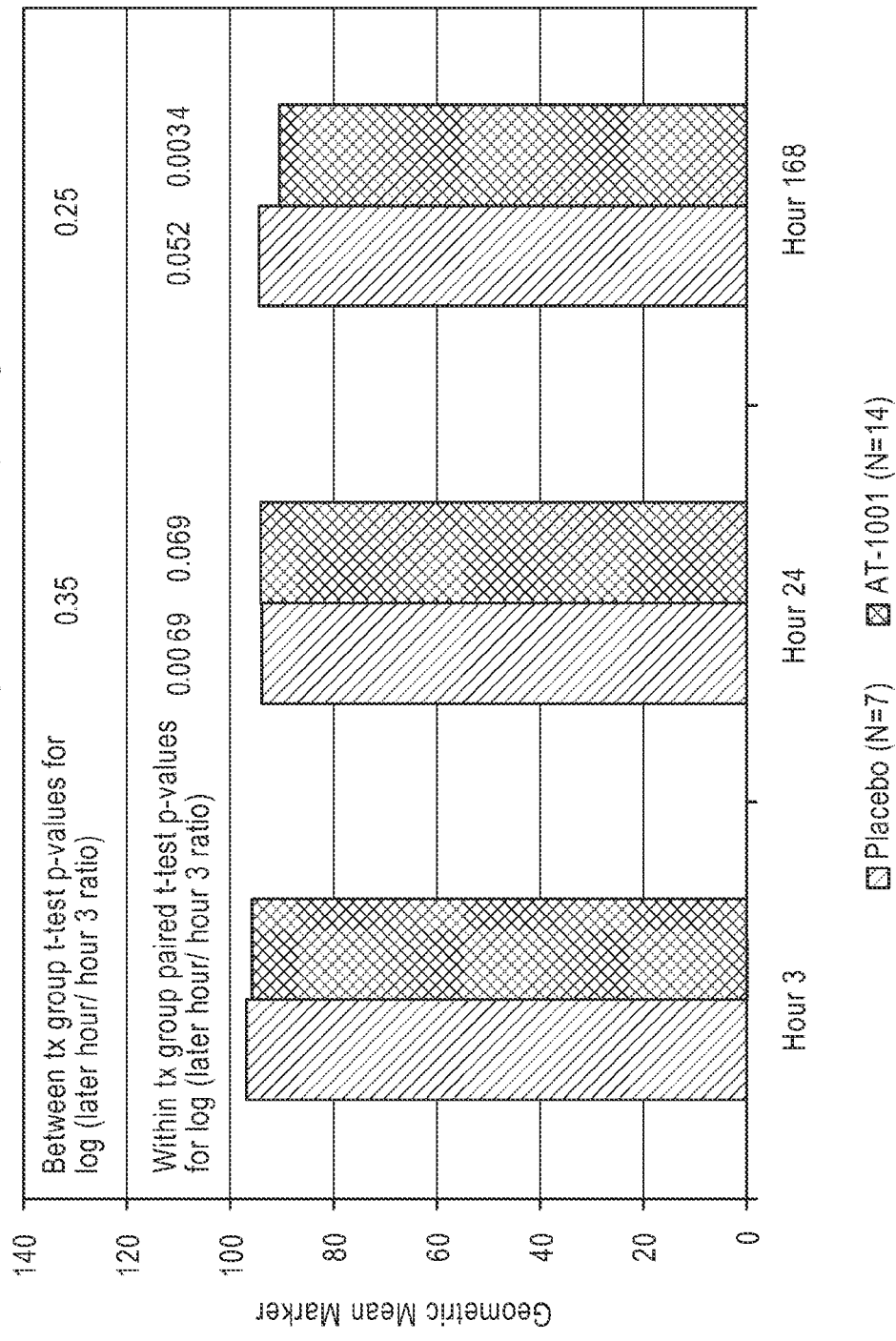
FIG. 9 is a bar graph showing % of cells expressing activation markers in placebo versus treatment on at hours 3, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.

HLA-DR expression on monocytes, measured by Mean Fluorescence Intensity (MFI) (FIG. 8) and by percentage of cells expressing (FIG. 9), was diminished more profoundly and at earlier time points in subjects in the AT-1001 group compared to subjects in the placebo group.

CD40, CD80 and CD86 markers (MFI and % expressing, lymphocytes and monocytes) were not significantly different between the AT-1001 and placebo groups and no trend was observed. CXCR3 expression was very low throughout the study period.

GI Symptom Diaries:

One patient in the placebo arm failed to complete the GI questionnaires throughout the study. Both the placebo and AT-1001 groups reported an increased GI urgency on Day 2, while on Day 3 only the placebo group remained elevated (p=0.061 vs. AT-1001 group). Frequency of bowel movements appeared higher in both groups on Day 2 and returned to baseline on Day 3, with no difference between groups, while reports of loose stools (liquid vs firm) was higher in the placebo group on Days 2 and 3 but failed to achieve statistical significance vs. AT-1001. VAS discomfort scores were consistently higher in the placebo group throughout the course of the study, but again failed to separate from the AT-1001 group with significance as shown in Table 7.

Celiac disease (CD) is an autoimmune enteropathy triggered by the ingestion of gluten containing grains (i.e.; wheat, barley, and rye) in genetically susceptible individuals. CD represents a unique model of autoimmunity for which, in contrast to other autoimmune diseases, the triggering environmental factor (gliadin), a close genetic association with HLA genes (DQ2 or DQ8), and a highly specific humoral autoimmune response (auto-antibodies to tissue transglutaminase) are well described. Despite the significant progress made in understanding the adaptive immunological aspects of CD pathogenesis, the early steps leading to the loss of tolerance and the development of the autoimmune process are still largely unknown. The complex interplay between genetic and environmental factors leading to the lack (or loss) of gluten tolerance is still poorly understood. Recent retrospective studies also suggest the importance of other factors, including intestinal infections, stressors and timing of gluten introduction in the diet of subjects genetically susceptible to CD, all of which affect intestinal paracellular permeability. Class II HLA genotypes DQ2 and DQ8 play a major predisposing role, being found in almost 100% of patients, but explain only 40% of the genetic risk of the disease (Van Heel, D. A. et al. Best Pract Res Clin Gastroenterol. 19:pp323-39 (2005)).

TABLE 7

Summary of Gastrointestinal Discomfort - VAS

| Variable | | Statistics/ Response Category | Placebo (N = 27) | AT-1001 (N =14) | P-Value* |
|---|---|---|---|---|---|
| Abdominal Pain/ Discomfort Today: 0 = No Pain, 10 = Worst Possible Pain | Day 1 | N | 6 | 14 | 0.32 |
| | | Mean | 1.3 | 0.6 | |
| | | Std | 2 | 1.1 | |
| | | Median | 0.5 | 0 | |
| | | Min | 0 | 0 | |
| | | Max | 5 | 3 | |
| | Day 2 | N | 6 | 14 | 0.26 |
| | | Mean | 4.5 | 2.6 | |
| | | Std | 4.7 | 2.8 | |
| | | Median | 4 | 1 | |
| | | Min | 0 | 0 | |
| | | Max | 10 | 9 | |
| | Day 3 | N | 6 | 14 | 0.17 |
| | | Mean | 1.7 | 0.7 | |
| | | Std | 2 | 1.1 | |
| | | Median | 1 | 0.5 | |
| | | Min | 0 | 0 | |
| | | Max | 5 | 4 | |

*t-test.

Patient Global Assessment:

The difference between groups in Patient Global Assessment ratings was insignificant as seen in Table 8.

TABLE 8

Summary of Patient Global Assessment of Change in Health Status Since Beginning the Study Medication

| Variable | Statistics/ Response Category | Placebo (N = 7) | AT-1001 (N = 14) | P-Value* |
|---|---|---|---|---|
| Patient global assessment | Minimally Improved | 0 ( 0%) | 1 ( 7%) | 0.41 |
| | No Change | 4 ( 57%) | 9 ( 64%) | |
| | Minimally Worse | 3 ( 43%) | 4 ( 29%) | |

*Cochran-Mantel-Haenszel test

While CD occurs as a result of an inappropriate T cell-mediated immune response against ingested gluten, a leaky gut is sine qua non with the disease and may be one of the primary non-HLA genetic risk factors of the disease (Monsour, A. J. et al. Nat Genet. 12:pp1032-41 (2005)). After crossing the intestinal epithelium, gliadin fragments are taken up and processed by APCs and presented to intestinal CD4 T cells. In vitro, it is known that gliadin fragments induce phenotypic and functional maturation of human dendritic cells, upregulating HLA-DR, CD80, CD83 and CD86 and down-regulating regulatory cytokines IL4, IL10 and TGF-β while the proinflammatory cytokines IL6, IL8, TNF-α are induced (Palova-Jelinkova, L. et al. J Immunol. 175:pp7038-45 (2005)). Moreover, a three day gluten challenge in celiac patients has been shown to induce a Th1 inflammatory state, as demonstrated by increased IFNγ at day 6 and expression of DQ2 restricted, gliadin-specific α4β7 T cells (Anderson, R. P. et al. Gut. 54:pp1217-23 (2005)).

The discovery of Vibrio cholerae-derived Zot has shed light on mechanisms involved in the modulation of the intestinal paracellular permeability and has allowed us to identify an intestinal mammalian analogue that participates in tj regulation. This protein analogue, that we have named zonulin, represents a eukaryotic paracrine signaling pathway that reversibly opens intestinal tj. We have demonstrated that zonulin expression is increased during early stages of CD and Type 1 diabetes (T1D), suggesting that the leaky gut reported at early stages of these diseases could be mediated by zonulin up-regulation.

The measurement of intestinal permeability needs to be interpreted in light of what we know about the physiology of the gastrointestinal tract. Different probes provide unique information about different segments of the GI tract, highlighting changes in surface area vs. changes in barrier state. The lactulose:mannitol ratio is used to quantify small intestinal permeability. An increased fractional excretion of lactulose suggests that there has been either small intestinal damage, or the opening of previously closed tight junctions. The fractional excretion of mannitol is proportional to villus tip surface area. Therefore, the lactulose:mannitol ratio is often interpreted as damage per unit are. In CD there is a reduction in small intestinal surface area (decrease in mannitol fractional excretion) and an increased opening of tight junctions or epithelial damage (increased lactulose fractional excretion) and both combine to increase the lactulose:mannitol ratio.

The subjects enrolled in this study appeared to be well controlled upon entry, as inferred from the normal small intestinal permeability on Day 1 as well as their low anti-TTG titres. However, with a single ingestion of gluten a significant increase in small intestinal permeability occurred in the placebo group that was not observed in the AT-1001 group. The increase in permeability observed in the placebo group was due to an increase in the fractional excretion of lactulose and a decrease in mannitol excretion that was abrogated by AT-1001. In summary, the initial protocol-specified analysis of this small study showed a benefit for AT-1001 in regard to the primary, a priori outcome that approached statistical significance.

The zonulin results confirmed prior in vitro and in vivo animal data showing that AT-1001 has no effect on zonulin release following gluten exposure. Rather, AT-1001 inhibitory effect is most likely related to its capacity to prevent zonulin binding to the target receptor, reducing submucosal exposure to gliadin and providing consequential indirect benefits on markers of immune activation.

AT-1001 appears to be not systemically available at therapeutic doses, as all plasma concentrations were BLQ (0.5 ng/ml). The most frequently reported AEs in this study, with the exception of headache, affected the gastrointestinal system. The incidence, severity, and causality of AEs were similar between the subjects administered AT-1001 and those administered placebo. Similarly, no major differences were observed in the AEs reported by male vs. female subjects; however, headache, which was one of the most commonly reported AEs, was only reported by female subjects. The high incidence of gastrointestinal AEs in this study is consistent with the symptoms that are often reported by CD patients when exposed to gluten. The AE data demonstrate that 12 mg AT-1001 was generally safe, well tolerated and effectively prevented the gluten induced gastrointestinal adverse events seen in the placebo group, although the relatively small sample size should be considered when analyzing the adverse event data. There seemed to be a trend in both treatment groups for more subjects to report a greater number of AEs on Day 2 after being administered study medication and ingesting 2.5 g of amygluten with their snack than after being administered study medication on Days 1 or 3 and ingesting a gluten-free snack. There were no other significant differences in AE reporting between groups (data on file).

The results of this study suggest that AT-1001 induced down-regulation of immunological markers that play an important role in establishing an immune response to antigens, as mirrored by HLA-DR down-regulation, in a manner consistent with the induction of so-called 'desensitization' or 'allergy'. The data suggest that AT-1001 may help to protect against immune stimuli from exposure to gliadin, by inducing anergy or tolerance. Activation markers, measured by mean fluorescent activity and % expressing cells were down-regulated by treatment with AT-1001 compared to placebo.

The following patents and patent applications are incorporated by reference: Formulations of zonulin antagonist are disclosed in U.S. provisional application Ser. No. 60/771,454, filed Feb. 9, 2006; Zonulin antagonists and uses are disclosed in U.S. Pat. No. 6,670,448; Method of diagnosing celiac disease disclosed in U.S. provisional patent application Ser. No. 60/836,988, filed: Aug. 11, 2006. As disclosed at paragraph [0025] of Provisional application Ser. No. 60/771,454, the composition is formulated for enteric delivery, and may comprise one or more delayed release coatings. A delayed release coating is typically substantially stable in gastric fluid and substantially unstable (e.g., dissolves rapidly or is physically unstable) in intestinal fluid, thus providing for substantial release of the tight junction effector from the composition in the duodenum or the jejunum.

While the invention has been described in detail, and with reference to specific embodiments thereof, it will be apparent to one of ordinary skill in the art that various changes and modifications can be made therein without departing from the spirit and scope thereof and such changes and modifications may be practiced within the scope of the appended claims. All patents and publications herein are incorporated by reference to the same extent as if each individual publication was specifically and individually indicated to be incorporated by reference in their entirety.

Example 2

A Phase 2a, Randomized, Double-Blind, Placebo Controlled, Dose Ranging, Multicenter Study to Determine the Safety, Tolerance, and Efficacy of AT-1001 in Celiac Disease Subjects during Gluten Challenge.

The study was conducted at up to 12 sites in the United States, and was anticipated to run between September and December 2006.

Objectives:

To demonstrate the safety and tolerability of multiple, oral doses of AT-1001 in celiac disease subjects that maintain a gluten-free diet.

To demonstrate the safety and tolerability of multiple, oral doses of AT-1001 in celiac disease subjects "in remission" [anti-tTG (−)≤10 EU].

To evaluate the efficacy of multiple dose levels of AT-1001 in preventing intestinal permeability changes induced by gluten challenge.

Measure change in urinary lactulose-to-mannitol (La/Ma) ratio from Day 0 to Day 14; a measure of intestinal permeability in response to gluten exposure.

A sub-chronic measure of injury/unit area vs. the acute drug exposure effect measured in Phase Ib To evaluate the effects of multiple dose levels of AT-1001 in preventing the induction of celiac disease signs and symptoms resulting from gluten challenge.

Methodology:

Seventy nine (79) subjects will be randomized to one of seven treatment regimens: drug placebo with gluten placebo, drug placebo with gluten, 0.25 mg AT-1001 with gluten, 1.0 mg AT-1001 with gluten, 4 mg AT-1001 with gluten, 8 mg AT-1001 with gluten, and 8 mg AT-1001 with gluten placebo. Study drug will be dispensed to subjects for fourteen (14) days of treatment. Study drug will be administered three times a day. AT-1001 or drug placebo will be administered 15 minutes prior to each meal (breakfast, lunch, and dinner). Gluten or gluten placebo will be taken during each meal. Subjects will remain on their gluten-free diet throughout the duration of the trial.

Study periods will include a 3 week screening period, 14 days of treatment, and a follow-up visit 7 days after completion of treatment. Study visits will include Screening, Day 0, Day 7, Day 14, and Day 21. The screening period will include medical history, physical examination, vital signs, clinical laboratory testing, and 12-lead electrocardiogram. Day 0 through Day 21 study visits will include vital signs, clinical laboratory testing, urine collection for intestinal permeability and nitrite/nitrate measurements and blood draws for PBMC collection, anti-tTG and zonulin measurements. Subjects will record daily and weekly responses to health assessment questionnaires in diaries. Adverse event reports will be monitored throughout the study.

Number of Subjects:
79 subjects
Diagnosis and Main Criteria for Inclusion:
Biopsy proven celiac disease
Gluten-free diet for ≥6 months
Anti-tTG≤10
Age 18 to 65 years.
Active Treatment:
AT-1001 capsules 0.25 mg with 800 mg gluten
AT-1001 capsules 1 mg with 800 mg gluten
AT-1001 capsules 4 mg with 800 mg gluten
AT-1001 capsules 8 mg with 800 mg gluten
AT-1001 capsules 8 mg with gluten placebo
Control Treatment:
Drug placebo capsules with 800 mg gluten
Drug placebo capsules with gluten placebo
Primary Outcomes:
Safety and Tolerance
Monitoring of adverse events (AEs)
Clinical laboratory testing of chemistry, hematology, and urinalysis specimens
Pregnancy Screening
EKG
Vital signs
Physical exam findings
AT-1001 plasma levels
Efficacy
The primary efficacy outcome is the Day 0-to-Day 14 change in urinary lactulose-to-mannitol (L-to-M) ratio, a measure of intestinal permeability as a response to gluten.
Secondary Outcomes:
Changes in subject's daily and weekly reported health outcomes
Changes in urinary lactulose-to-mannitol (L-to-M) ratios between Day 0 to Day 7
Changes in urinary lactulose fractional excretion between Day 0 to Day 7 to Day 14
Changes in urinary mannitol fractional excretion between Day 0 to Day 7 to Day 14
Changes in urinary nitrite/nitrate excretion between Day 0 and Day 14
Changes in Anti-Tissue Transglutaminase (anti-tTG) levels between Screening and Day 21
Changes in cell markers and cytokines from PBMCs
Changes in zonulin levels
Statistical Methods/Statistical Analysis Plan:
Primary Outcomes
Safety Evaluation:

All subjects who receive treatment and have a subsequent safety evaluation will be included in the safety analyses. All adverse events reported during the study will be listed, documenting course, severity, and outcome. Adverse events will be summarized by treatment, the MedDRA system organ class, and maximum severity. Laboratory parameters, vital signs, EKG assessments, and physical exam results will be summarized with descriptive statistics as appropriate.

Efficacy Evaluation:

The analysis of the primary outcome will include a table of the GM L-to-M ratios (Days 0 and 14), for each dosage group, including placebo and the (no challenge, no AT-1001) group. Additionally, the GM Day 0-to-Day 14 ratios of the L-to-M ratios, with confidence bounds, will be provided for each comparison of an active AT-1001 dosage to placebo and of the two placebo groups. The primary analysis will use ANOVA to compare the placebo group to each dose group, using a standard multiple comparison method. The focus would be on identification of one or more statistically significant test doses.

Secondary Outcomes
Patient's daily and weekly reported health outcomes
Lactulose-to-mannitol (L-to-M) ratios
Lactulose and mannitol fractional excretion
Nitrite/nitrate
Anti-Tissue Transglutaminase (tTG) levels
PBMC cytokines and cell markers
Zonulin levels Continuous secondary analyses will be carried out in the same fashion as the primary analyses.

LIST OF ABBREVIATIONS AND DEFINITIONS OF TERMS

AE Adverse event
μg Microgram
ANOVA Analysis of variance
AUC Area under the curve
BMI Body Mass Index
BP Blood pressure
CFR United States Code of Federal Regulation
cGCP Current Good Clinical Practice
Cmax Concentration maximum
CRF Case Report Form
dL Deciliter
EKG Electrocardiogram
ETOH Ethanol
FITC Fluorescein-isothiocyanate
gm gram
GM Geometric Mean
βhCG Beta human chorionic gonadotropin
HIV Human Immunodeficiency Virus
HLA Human leukocyte antigen
HPLC High Performance Liquid Crystallography
ICH International Conference on Harmonization
IEC Independent Ethics Committee
IFN gamma Interferon gamma
IP Intestinal permeability
ISR International Safety Surveillance Report
IV Intravenous
kg Kilogram
mg Milligram
ml Milliliter
ng Nanogram
NPO Nothing by mouth
pK Pharmacokinetic
PBMC Peripheral Blood Mononuclear Cell
Rt Resistance
SAE Serious adverse event
SMC Safety Monitoring Committee
T½ Half life
T1D Type 1 diabetes
TID Three times a day
Tmax Time maximum
ZOT Zonula occludens toxin

INTRODUCTION/BACKGROUND

Zonulin is an endogenous substance that appears to regulate endothelial cell tight junction function in animals and in humans [1-4]. Gluten is the major protein fraction that is found in the cereals wheat, rye and barley. In USA and Europe gluten is a major component of the diet of normal individuals, given the high consumption of wheat-derived, gluten-rich products such as bread, pasta and pizza. In vitro, ex vivo, and in vivo animal experiments suggest that gluten and/or its derivative fraction gliadin are one possible environmental trigger causing zonulin release and changes in intestinal barrier function [5-11]. Data obtained in celiac patients, their first degree relatives, and the first degree relatives of type-1 diabetes (T1D) patients is consistent with this effect. In addition, retrospective data suggest that zonulin up-regulation (and, therefore, changes in intestinal permeability) is more pronounced in subjects with the HLA DQ2 genotype.

AT-1001 is an octapeptide zonulin receptor antagonist. The initial drug product is a multi-particulate oral formulation with a locus of activity limited to the luminal surface of the small intestine. At supra-therapeutic dosing in animals, the product is not systemically absorbed to any significant extent and is devoid of significant systemic toxicities. AT-1001 will be administered (at least) TID before meals and used to reverse the elevated intestinal permeability which is seen in many autoimmune diseases, including Celiac Disease, Primary Biliary Cirrhosis, Autoimmune Hepatitis and Type-I Diabetes Mellitus. Experiments with ex vivo human tissue and in mice demonstrate that AT-1001 blocks zonulin binding to its receptor, completely inhibits the peak of F-actin increment induced by gliadin, and completely inhibits the gliadin induced reduction in intestinal Rt (resistance) [4,5,10]. Fluorescent FITC labeling demonstrated that measurable amounts of the antagonist do not cross into the submucosa or the vasculature. Pretreatment with the peptide fails to inhibit gliadin induced zonulin release, confirming that AT-1001 exerts its inhibitory effect on gliadin induced actin polymerisation by blocking the zonulin receptor rather than affecting zonulin release. Administration of gliadin and/or ZOT and zonulin analogues in the presence of AT-1001 fail to significantly reduce intestinal resistivity, confirming the effect of the molecule is specific to the zonulin receptor [4,5].

This study will establish the safety and the effects of multiple doses of oral AT-1001 on intestinal permeability in subjects with celiac disease who have been gluten free for >6 months and demonstrated to be in remission, and who will subsequently be challenged with gluten. Data from this study will be utilized to support future safety and efficacy investigations in humans.

Non Clinical Experience With AT-1001

Toxicity studies have been performed in rats and Beagle dogs. In a single dose study in rats, AT-1001 was administered intravenously at up to 5 mg/kg. There were no clinical observations, clinical chemistry changes, or gross postmortem observations associated with IV dosing of AT-1001 at any dose level. In a 14 day repeat-dose study in rats, AT-1001 was administered by oral gavage once daily for 14 days at doses up to 1000 mg/kg. There were no treatment-related clinical observations, clinical pathology changes, body weight or weight gain changes, organ weight changes, or gross or microscopic tissue changes associated with repeated oral dosing of AT-1001 at any dose level. In a second repeat-dose study, rats received oral AT-1001 once daily for 28 days at up to 1000 mg/kg. No treatment-related deaths occurred. Food consumption, body weights/gains, ophthalmic observations were unaffected by treatment. In a recovery group, body weight gain was lower in the dose males at week 8 (recovery week 4). Any alterations in clinical chemistry, hematology, coagulation, urinalysis and organ weight data were considered coincidental based on absence of dose-response relationships and absence of histopathological changes. No gross necropsy or histopathology findings were considered to be treatment-related.

In a single-dose 14 day study in Beagle dogs, dogs were administered a single dose of up to 5 mg/kg intravenously and observed for 14 days. The clinical chemistry and hematology profiles were unremarkable and no signs of toxicity were observed. In a two-dose study, dogs were administered AT-1001 in enteric-coated beads at 20 mg/kg on day 1, followed by 40 mg/kg on day 2. Total protein and globulin levels appeared to be slightly elevated 24 hr after administration of the 40 mg/kg dose with a corollary decrease in A/G ratios noted. No other alterations in serum clinical chemistry parameters were evident and no clinical signs of toxicity were noted during the study. In a multiple dose study, dogs were administered AT-1001 in enteric-coated beads orally at up to 9 mg/kg daily for 4 weeks. No treatment-related deaths occurred and all dogs appeared normal throughout the study. Body weights, body weight gains, ophthalmic observations and EKG readings were unaffected by treatment. Any alterations in clinical pathology profiles were considered coincidental in nature. No alterations in absolute or relative organ weight data were detected. None of the gross necropsy or histopathology findings were considered to be treatment-related.

Two in vitro genotoxicity studies have been performed. In an Ames test (bacterial reverse mutation assay), *Salmonella* and *E. coli* strains were tested with AT-1001 at up to 5000 μg per plate. AT-1001 was negative for mutagenic activity, with and without metabolic activation. In an in vitro chromosome aberration study with human peripheral lymphocytes, AT-1001 was tested at concentrations up to 1200 μg. AT-1001 was negative for inducing structural or numerical chromosome aberrations in human peripheral lymphocytes with and without metabolic activation.

Two safety pharmacology studies for cardiotoxicity effects have been performed. A hERG test was performed to assess the in vitro effects of AT-1001 at up to 1 ng/mL on the potassium selective $IK_r$ current generated in normoxic conditions in stably transfected HEK 203 cells. None of the concentrations of AT-1001 caused statistically significant effects. In a study on the cardiovascular effects of AT-1001 was administered to unconscious female rabbits, hemodynamic and electrocardiography measurements were monitored during the study and evaluated. There were no notable effects of intravenous AT-1001 administration on the EKG, at doses up to 1 mg/kg.

Clinical Experience With AT-1001

AT-1001 has been tested in 2 clinical trials with healthy subjects, a single dose and a multi-dose safety trial, and in a third Proof of Concept trial in subjects with celiac disease. A final clinical study report has been written for the single dose trial and a draft clinical study report for the multi-dose and Proof of Concept trials has been written.

The single dose trial was a double-blind, placebo controlled, randomized trial of 24 healthy adults. Three (3) cohorts of 8 subjects each received AT-1001 doses of 3, 12, or 36 mg or placebo. There were no serious adverse events (SAEs) reported in this study and none of the subjects were discontinued from the study due to an AE. Excluding a single episode of nausea following placebo, all Treatment Emergent Adverse Events (TEAE's) were mild or moderate in severity. All AEs reported in this study resolved without concomitant therapy. Headache was the most common AE experienced, reported one time each by 3 (13%) subjects.

One subject experienced an elevated urine white blood cell count that remained elevated on recheck; however, the subject was lost to follow-up for a subsequent recheck. No clinically significant treatment-related trends were observed regarding clinical laboratory, vital sign, EKG, or physical examination assessments with respect to subject safety.

AT-1001 plasma drug levels were measured in all three cohorts at baseline, 0.25, 0.75, 1.25, 1.75, 2.25, 3.25, 4, 5, and 8 hours post dose. All results were below the limits of quantification (0.5 ng/ml) of the validated AT-1001 plasma assay utilizing HPLC MS-MS.

The multi-dose trial was a double-blind, placebo controlled, randomized trial of 24 healthy adults. Three (3) cohorts of 8 subjects each received AT-1001 doses of 250 μg, 1, or 4 mg or placebo three times a day. There were no serious adverse events (SAEs) reported in this study and none of the subjects were discontinued from the study due to an AE. Reported AEs were all mild and headache was the most common AE.

The Proof of Concept trial was a double-blind, placebo controlled, randomized trial of 21 subjects with celiac disease. Subjects received single doses of 12 mg AT-1001 or placebo for three days and were challenged once with gluten. There were no serious adverse events (SAEs) reported in this study and none of the subjects were discontinued from the study due to an AE. The majority of AEs were mild, a few were moderate, and none were severe. Headache was the most common AE. Other common AEs were nausea, flatulence, and diarrhea; however, these symptoms may be related to the gluten challenge.

Study Objectives

To demonstrate the safety and tolerability of multiple, oral doses of AT-1001 in celiac disease subjects that maintain a gluten-free diet.

To evaluate the efficacy of multiple dose levels of AT-1001 in preventing intestinal permeability changes induced by gluten challenge.

To evaluate the effects of multiple dose levels of AT-1001 in preventing the induction of celiac disease signs and symptoms resulting from gluten challenge.

Study Design

Figure 10:
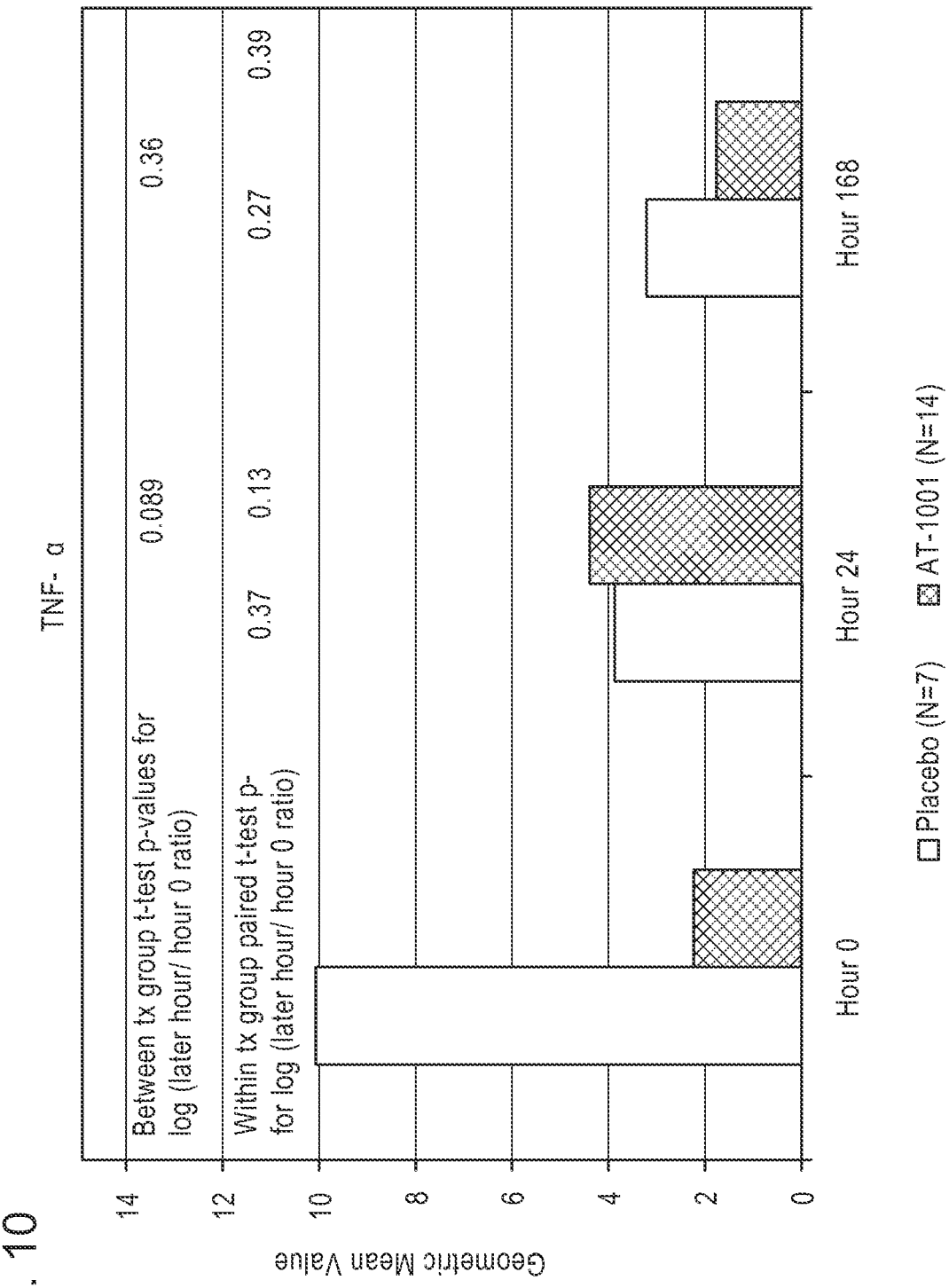
FIG. 10 is a bar graph showing TNFα concentration in placebo versus treatment on at hours 0, 24 and 168 in subjects enrolled in an inpatient, double-blind, randomized placebo controlled study to determine the safety, tolerability, pharmacokinetic and pharmacodynamic effects of 12 mg doses of AT-1001 in CD subjects.
Figure 11:
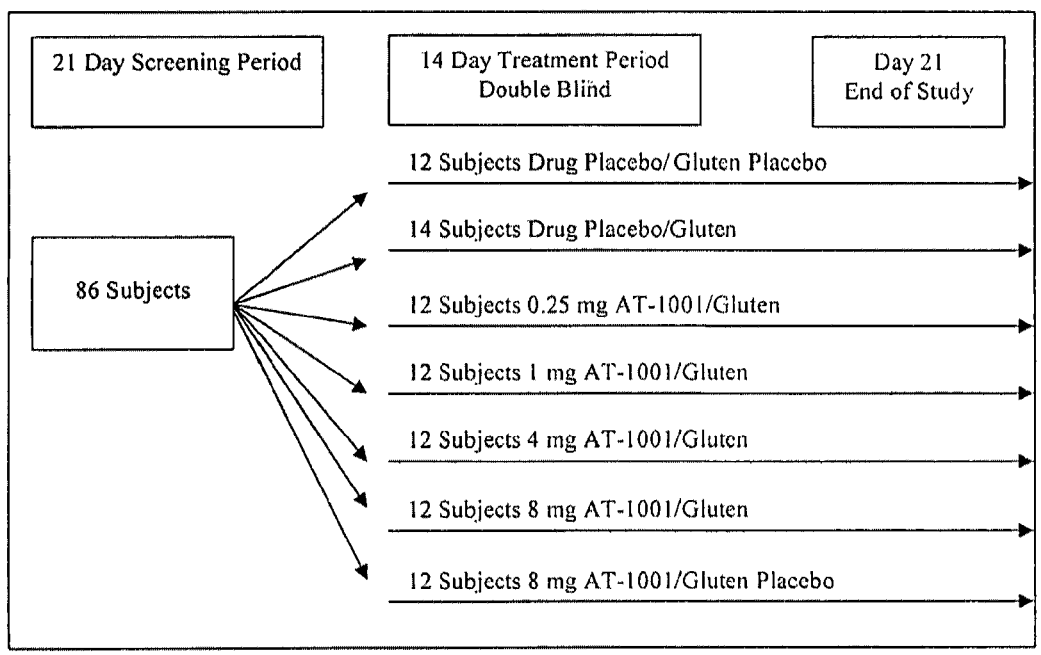
FIG. 11 is a depiction of the treatment schedule for (79) subjects enrolled in a randomized, double-blind, placebo controlled, dose ranging Phase 2a study to determine the safety, tolerance, and efficacy of AT-1001 in Celiac Disease subjects during gluten challenge.
Figure 12:
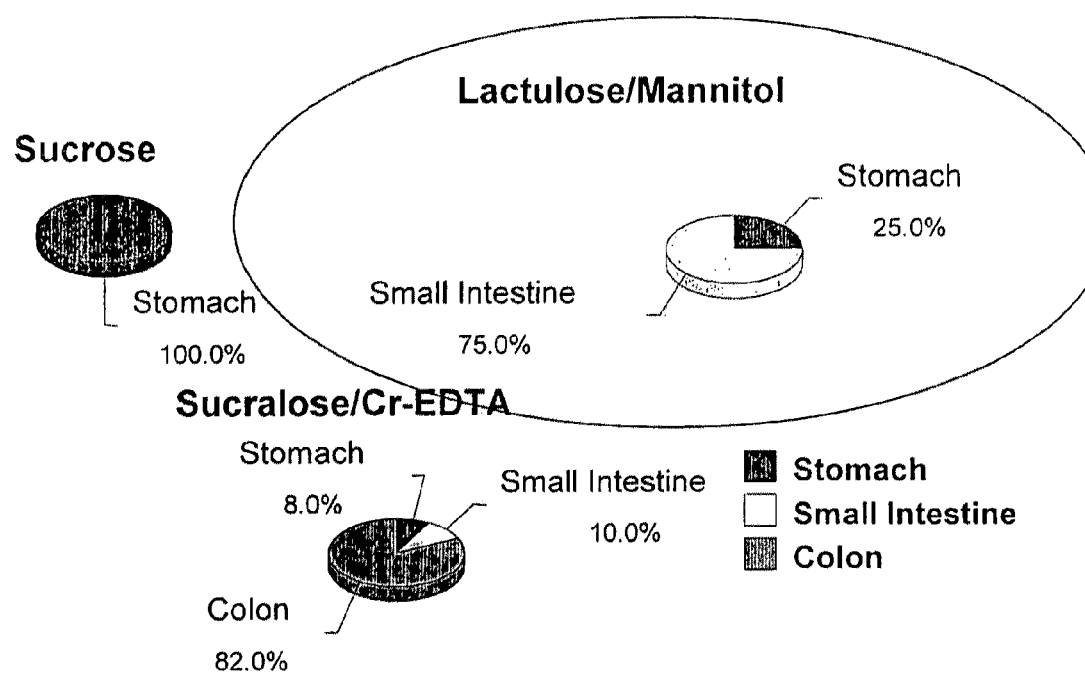
FIG. 12 is a schematic describing the interpretation of Lactulose/Mannitol clearance data.
Figure 13:
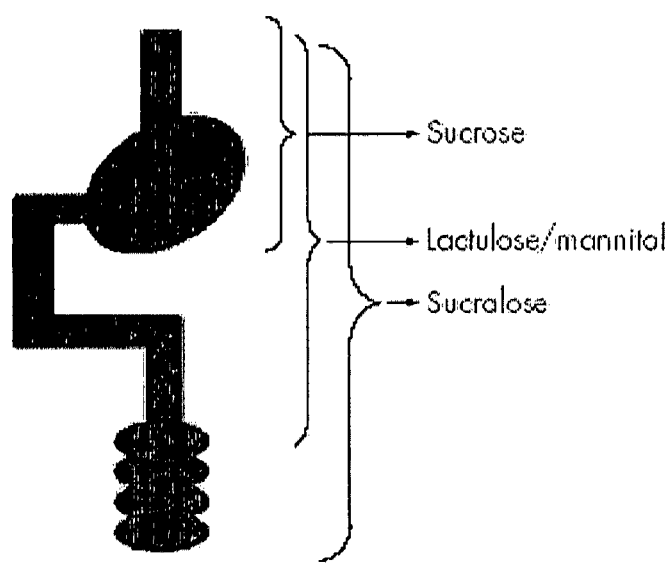
FIG. 13 is a schematic depiction of Sucrose, Lactulose/Mannitol and Sucralose absorption in the gastrointestinal tract.
Figure 14:
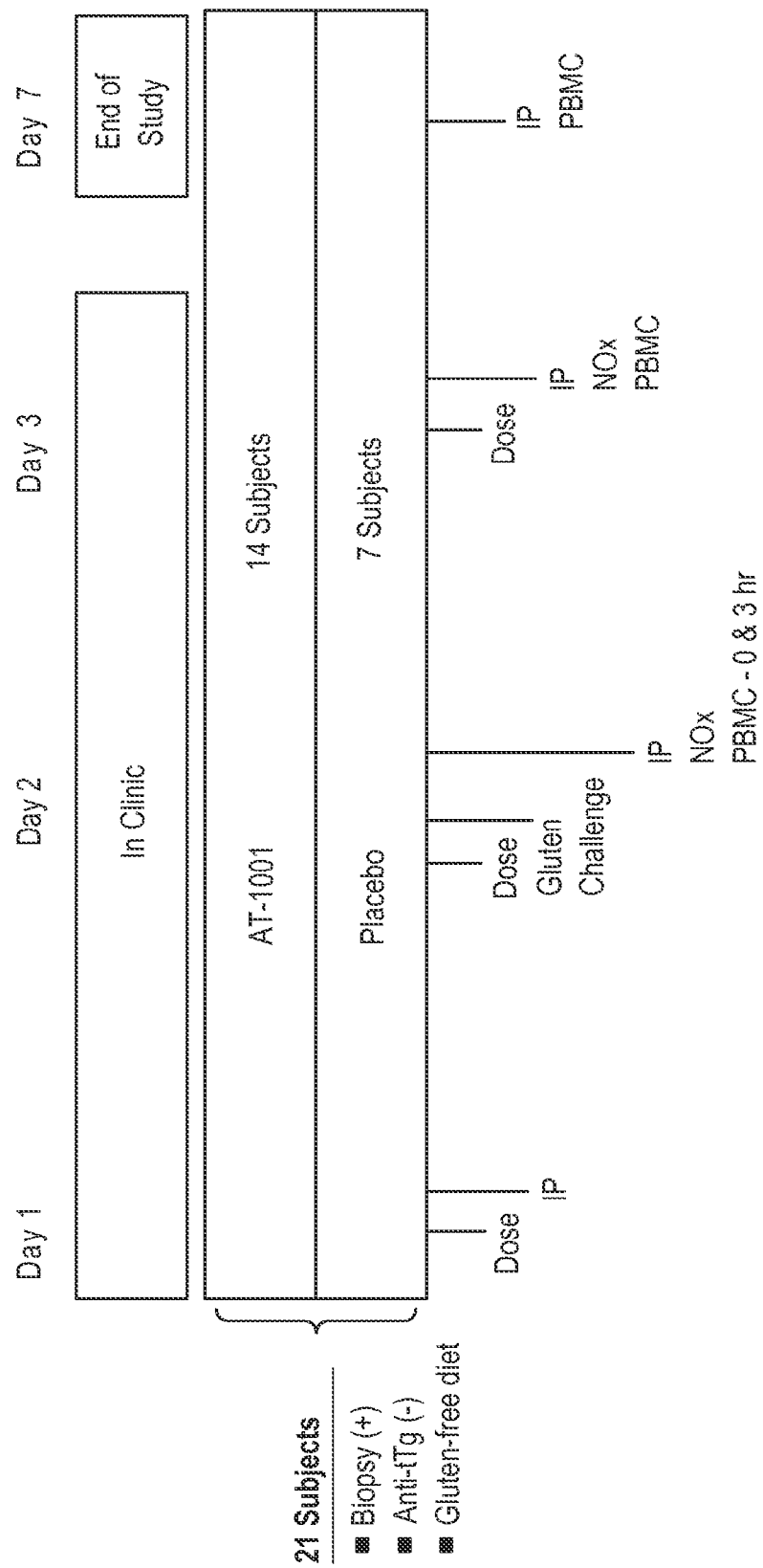
FIG. 14 is a depiction of the Phase Ib Proof Of Concept Trial Design. Day 1 procedures were carried out over 30 minutes; Day 2 procedures were carried out over 60 minutes; and Day 3 procedures were carried out over 30 minutes.
Figure 15:
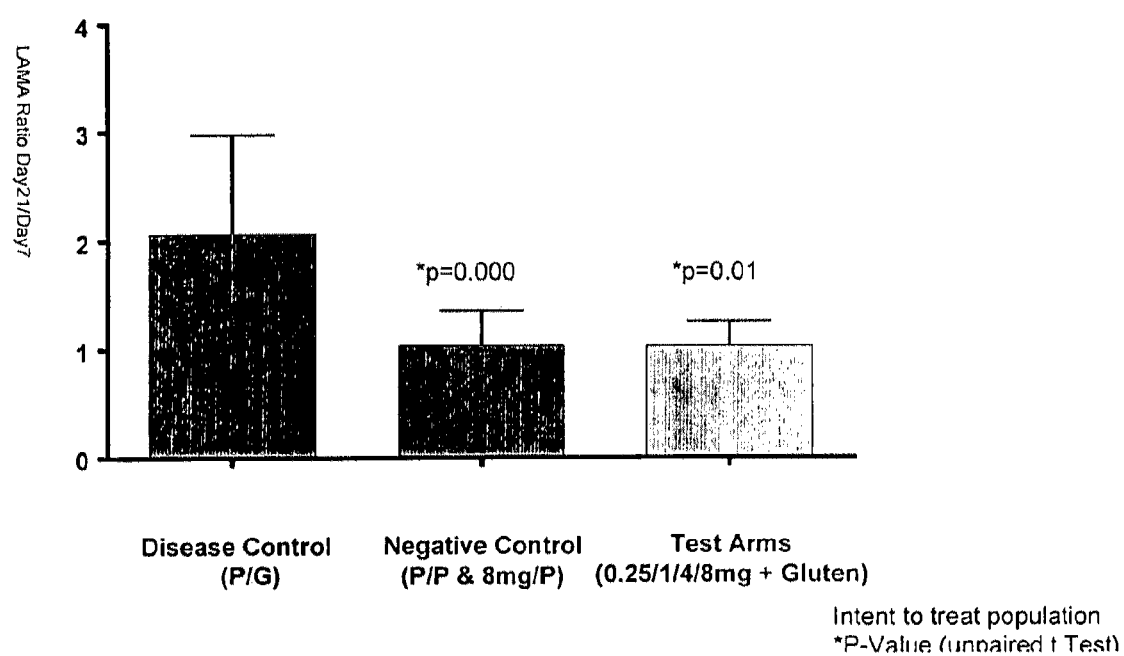
FIG. 15 is shows the ration of Lactulose/Mannitol clearance at day 21 versus day 7 for each of the aggregate groups of a Phase 2a study to determine the safety, tolerance, and efficacy of AT-1001 in Celiac Disease subjects during gluten challenge.
Figure 16:
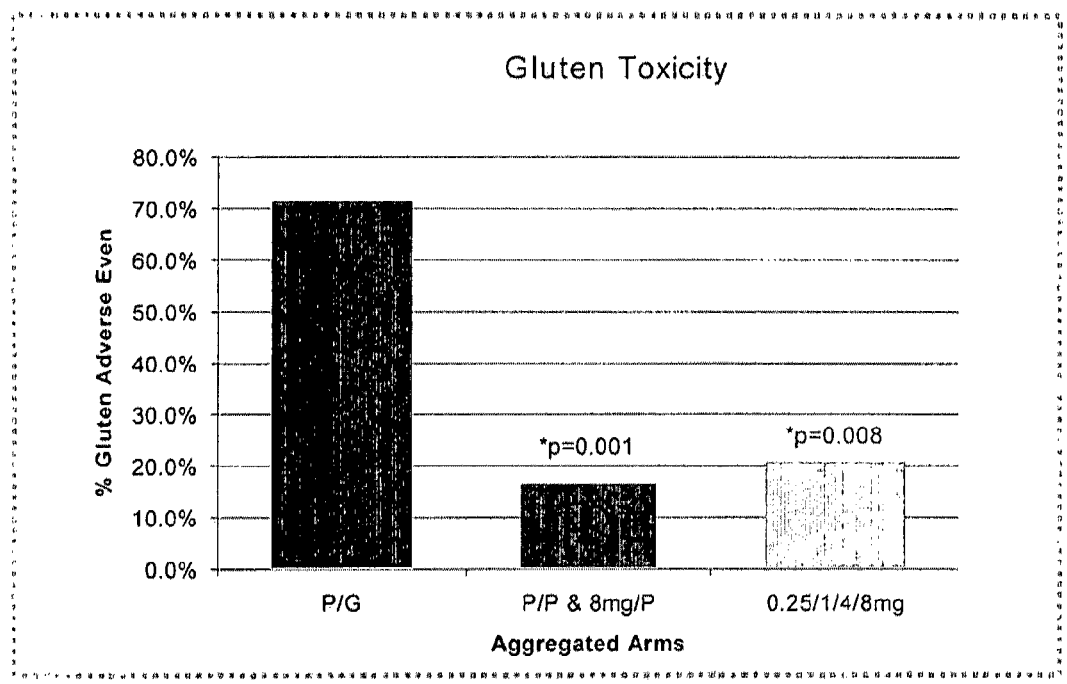
FIG. 16 shows analysis of adverse events for each of the aggregate groups of a Phase 2a study to determine the safety, tolerance, and efficacy of AT-1001 in Celiac Disease subjects during gluten challenge. P-Value (Fisher's Exact Test Treatment emergent Gluten AE's include: Dermatitis Herpetiformis, diarrhea, elevated LFTs, nausea (with other symptoms), gas, abdominal pain, aphthous ulcers and dyspepsia.
Figure 17:
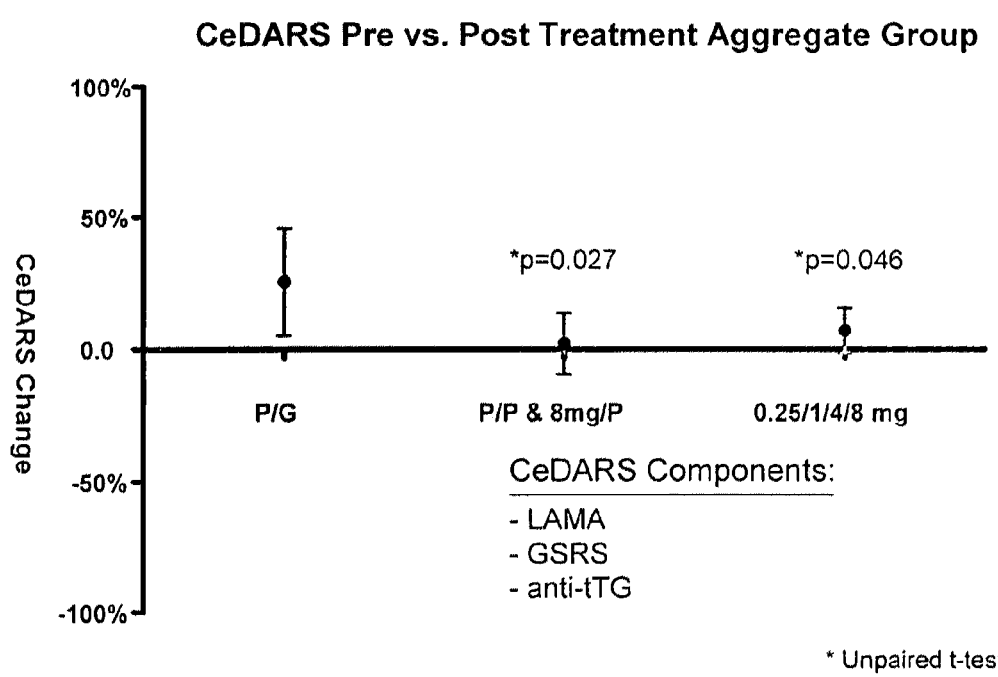
FIG. 17 shows a retrospective analysis of CeDARS index scores for of the aggregate groups of a Phase 2a study to determine the safety, tolerance, and efficacy of AT-1001 in Celiac Disease subjects during gluten challenge.

Seventy nine (79) subjects will be enrolled in this multi-center, randomized, double-blind, placebo controlled study. Subjects will be assigned to treatment groups according to the schedule described in FIG. 10.

Treatment Summary

According to a randomized, double-blind design subjects will receive AT-1001 or matching drug placebo and challenge with gluten or gluten placebo. AT-1001 will be administered as capsules containing enteric coated, multi-particulate beads with a dose of 0.25, 1, 4, or 8 mg. Gluten will be administered as 2 capsules each containing 400 mg of amygluten powder and gluten placebo will contain a matching amount of corn starch.

Study Timetable

Subjects will have a screening visit up to three weeks prior to the first dose to ensure eligibility for study participation. Day 0 subjects will be randomized to a treatment regimen. On Day 1 with the morning meal, subjects will begin treatment with AT-1001/placebo and gluten/gluten placebo. Subjects will continue their treatment regimen until their Day 14 visit. An End of Study visit will occur one week later on Day 21.

Diaries will be provided to subjects on Day 0 with instructions on use of the diaries and completing the questionnaires. Collection of information in the diaries will continue through Day 21.

Selection of Study Population

Male or female volunteers between the ages 18 and 65 years with celiac disease.

Number of Subjects

Seventy nine (79) subjects will be enrolled into the study.

Inclusion Criteria

Eligible subjects must meet the following criteria before being enrolled into the study:

Between 18 and 65 years of age.

Subject must have been diagnosed with celiac disease by biopsy for >6 months (attending physician confirmation will be accepted in lieu of a biopsy report).

Subject has Anti-Tissue Transglutaminase (tTG)<10 EU as measured by serology.

Subject must be on a gluten-free diet for at least the past 6 months.

Female subjects should be either post-menopausal (amenorrhea for at least 24 consecutive months), surgically sterile, or women of child-bearing potential (WOCP) with a negative serum beta human chorionic gonadotropin (HCG) pregnancy test prior to entering the study and who are using or agree to use acceptable methods of contraception. Abstinence is acceptable as long as they agree to use contraception if they are sexually active. Acceptable contraceptives include intrauterine devices (IUDs), hormonal contraceptives (oral, depot, patch or injectable) in use for one month prior to screening and double barrier methods such as condoms or diaphragms with spermicidal gel or foam.

Subject must sign an Institutional Review Board approved informed consent and agree to complete required clinic visits.

BMI between 18.5 and 38.

Exclusion Criteria

Subjects meeting the following criteria are not eligible for the study:

Subject has any food intolerances or food allergies (other than celiac disease) that would interfere with the conduct of the study (e.g. corn starch).

Subject has any chronic active GI disease other than celiac disease (e.g., IBS, Crohn's, Colitis).

Subject has diabetes (Type 1 or Type 2).

Subject is currently taking an excluded medication (see section 6.3).

Subject chronically consumes non-steroidal anti-inflammatory agents ("NSAIDs")

Subject is currently taking proton-pump inhibitors.

Subject has consumed≥3 fl oz. of alcohol within 2 days of each treatment visit (Day 0, 7, 14, and 21).

Subjects with symptomatic neurological disease(s).

Subjects who smoke or use nicotine or nicotine containing products. Ex-smokers must have stopped smoking or must have stopped using tobacco and/or nicotine-containing products for at least 6 months prior to entry into the study.

Subject has clinically significant abnormal laboratory test results at the screening visit as determined by the Principal Investigator and consented by Alba's Medical Monitor.

Subject is pregnant or breast feeding.

Subject is sexually active without contraception.

Subject has donated blood within the last 56 days.

Subject has donated a unit of plasma in the last 7 days.

Subject has hemoglobin value below 10.5 g/dL.

Subject has history of alcohol or drug abuse in past 2 years.

Subject has a positive urine drug test at screening.

Subject has a positive HIV, Hepatitis B surface antigen or Hepatitis C test.

Subject has participated in any active drug study within the past 30 days.

Subject is deemed inappropriate by the Principal Investigator.

Study Plan

Study Procedures

A table of study procedures can be found in Table 12.

Entry Into Study

All subjects who sign an Informed Consent will be assigned a unique screening number. This number will be used for identification purposes prior to randomization on Visit 2. All subjects who sign an Informed Consent but do not enter the study must have a reason recorded as to why they were not randomized into the study. This information will be recorded in a log maintained in the Investigator's study binder.

After confirming eligibility on Visit 2, the subject will be assigned a unique 5-digit subject number. Subject identification numbers will consist of a 2-digit site number followed by a 3-digit subject ID number. The 3-digit subject ID numbers will be assigned sequentially at each site beginning with #001. A log documenting all assigned subject identification numbers with subject's initials, date of birth, and date of randomization, must be maintained in the investigator's study binder for inspection by the SPONSOR.

Visit Specific Study Procedures

Visit 1 (Screening, 3 weeks)

Perform informed consent

Review inclusion/exclusion criteria

Document medical history

Document menstrual history and pregnancy screening, including serum pregnancy test for females Document concurrent medications (including prescription and over-the-counter medications taken within 30 days of screening)

Perform physical examination including 12-lead electrocardiogram, vital signs, height, and weight Collect blood and urine specimens for clinical laboratory testing (see Section 8.4 for specific testing to be performed)

Collect urine for drug screening (see Section 8.4 for specific testing to be performed)

Collect serum for anti-tissue transglutaminase (tTG) testing

Collect blood for HIV, Hepatitis B surface antigen, and Hepatitis C testing

When screening clinical laboratory test results are received, they must be reviewed by the Principal Investigator for clinically significant abnormalities. If no clinically significant abnormalities are found the subject should be scheduled for dosing. If clinically significant abnormalities are found retesting of the subject will be at the discretion of the Principal Investigator in consultation with the Sponsor.

Visit 2 (Day 0, within 21+2 days from screening)

Confirm inclusion/exclusion criteria

Monitor for concurrent medications

Perform urine pregnancy test on female subjects

Randomize subject

Provide diaries and instructions to subjects

Subject completes baseline weekly diaries (Health and GI outcome)

Monitor vital signs (BP and pulse)

Perform 12-lead electrocardiogram

Conduct physical exam

Collect specimens for clinical laboratory testing (chemistry, hematology, and urinalysis)

Collect plasma sample for AT-1001

Collect serum zonulin sample

Collect PBMC samples

Collect spot urine for nitrite/nitrate sample

Ensure subject has fasted for at least 4 hours (NPO except water) then administer intestinal permeability test Dispense study drug (subjects will begin administration on Day 1 with breakfast and continue dosing up to Day 14 visit)

Provide intestinal permeability kit and instructions to subject for next visit

Remind subjects to complete daily diaries every night

Day before Visit 3
Contact subject and remind them to perform intestinal permeability test
Visit 3 (Day 7 +/−1 day)
Subject completes Health and GI outcome assessments
Collect overnight urine sample
Monitor for adverse events
Monitor for concurrent medications
Monitor vital signs (BP and pulse)
Collect specimens for clinical laboratory testing (chemistry, hematology, and urinalysis)
Collect plasma sample for AT-1001
Collect PBMC samples
Provide Intestinal Permeability kit and instructions to subject
Day before Visit 4
Contact subject and remind them to perform intestinal permeability test
Visit 4 (Day 14 +/−1 day)
Subject completes Health and GI outcome assessments
Collect overnight urine sample
Monitor for adverse events
Monitor for concurrent medications
Monitor vital signs (BP and pulse)
Collect specimens for clinical laboratory testing (chemistry, hematology, and urinalysis)
Collect plasma sample for AT-1001
Collect serum zonulin sample
Collect PBMC samples
Collect spot urine for nitrite/nitrate sample
Provide intestinal permeability kits and instructions to subject
Day before Visit 5
Contact subject and remind them to perform intestinal permeability test
Visit 5 (Day 21 +/−2 days)
Subject completes Health and GI outcome assessments
Collect overnight urine sample
Monitor for adverse events
Monitor for concurrent medications
Monitor vital signs (BP and pulse)
Perform 12-lead electrocardiogram
Conduct physical exam
Collect specimens for clinical laboratory testing (chemistry, hematology, and urinalysis)
Collect serum for pregnancy test on female subjects
Collect serum for anti-tissue transglutaminase (tTG) sample
Collect serum zonulin sample
Collect PBMC samples
All clinically significant adverse events present at the end of study visit should be followed until resolution or diagnosis can be made.
Subject Restrictions During Study
Subjects must be willing to return for all scheduled study visits.
Subjects must refrain from illicit drug use throughout the duration of the study.
Subjects must refrain from consuming >3 fluid ounces of alcohol use within 2 days of each treatment visit.
Concomitant Medications
Subjects taking the following medications will not be eligible:
Bismuth containing medications (e.g., Pepto-Bismol)
Any Antibiotics
Loperamide (eg., Imodium® A-D)
Diphenoxylate containing medications (e.g., Lomotil)
Proton pump inhibitors
NSAIDs (all, including aspirin)
Immune suppressants (incl. Dapsone)
Pancreatic enzyme replacement
Oral Corticosteroids (e.g., Entocort)
Fibrates
Amphetamines (e.g., ADHD meds)
Zetia
Withdrawal Criteria
Reasons for withdrawal may include but are not limited to the following:
Either at the Investigator's request, for safety reasons, such as severe adverse reactions, or at the subject's request.
When the requirements of the protocol are not followed.
When a concomitant therapy liable to interfere with the results of the study is reported, or required, by the subject (the Investigator will report all such information on the CRFs and decide, in accordance with the Sponsor, whether the subject is to be withdrawn).
All premature discontinuations and their causes must be carefully documented by the Investigator on the End of Study CRF, and, if need be, on the Adverse Event form.
If, for any reason, a subject is dropped before completing the final visit, the reason for termination will be entered on the End of Study CRF. All data gathered on the subject prior to termination will be made available to the Sponsor. Subjects not completing the entire study should be fully evaluated when possible. The appropriate CRFs should be completed in addition to the End of Study CRF.
Reasons for study completion/discontinuation as listed on the End of Study CRF are defined as follows in Table 9:

TABLE 9

| Reasons for Study Completion/Discontinuation | |
|---|---|
| Normal Study Completion | Subject completes the study as planned in the protocol. |
| Adverse Event | Subject withdrew from the study early due to an adverse event. Complete Adverse Event form. |
| Subject Request | Subject withdrew consent and terminated the study early. Explain in comments on CRF. |
| Protocol Violation | Investigator wishes to terminate the subject due to a protocol violation. Site monitor or Sponsor should be contacted the before making decision. Explain in comments on CRF. |
| Other | Any other reason for early subject withdrawal. Explain in comments |

All subjects are free to withdraw from participating in this study at any time and for whatever reason, specified or unspecified, and without prejudice.
Blinding
This study will be conducted as a double-blind study to avoid biased assessments of adverse events. The subject, investigator, clinic staff responsible for reviewing all safety data with the subject, and SPONSOR staff responsible for the day to day conduct of the study are blinded and will not know the treatment assignment the subject has been administered. In the event a subject's treatment assignment becomes known to any blinded study team member, the SPONSOR must be notified immediately by the Investigator.
Efficacy Assessments
In-vivo intestinal permeability assays
On Days 0, 6, 13, and 20 subjects will drink a solution of lactulose and mannitol. Subject's urine will be collected during the day on Day 0 and overnight prior to subsequent visits and analyzed for lactulose and mannitol recoveries via standardized methodologies. Lactulose:mannitol (recovered) ratios will then be used to quantify paracellular permeabilities for each subject's collection.

Daily and Weekly Questionnaires

At bedtime from Day 0 through Day 20, subjects will record their level of GI symptoms in their diary (Appendix C).

On Day 0, 7, 14, and 21 subjects will complete two weekly questionnaires in their diaries, the Psychological General Well-Being Index (PGWBI) and the Gastrointestinal Symptom Rating Scale (GSRS) (Appendix D).

Nitrite/Nitrate Levels

On Days 0 and 14 a spot urine sample will be collected for nitrite/nitrate determinations. Nitrite/nitrate levels will be assessed for correlation to the measures of intestinal permeability (lactulose and mannitol).

Anti-Tissue Transglutaminase (Anti-tTG)

On Screening and Day 21 serum will be collected for Anti-Tissue Transglutaminase (anti-tTG) antibodies. Changes between screening and Day 21 will be assessed for correlation to the measures of intestinal permeability (lactulose and mannitol).

PBMC

On Days 0, 7, 14 and 21 blood will be drawn for PBMC collection. Cytokine and cell surface marker determinations will be measured. Cytokine levels and cell surface markers will be assessed for correlation to the measures of intestinal permeability (lactulose and mannitol).

Zonulin Levels

On Days 0, 7, 14, and 21 subjects will have serum drawn for zonulin determinations. Serum zonulin levels will be assessed for correlation to the measures of intestinal permeability (lactulose and mannitol).

Safety Assessments

In addition to adverse event monitoring (see Section 10), the following procedures must be performed at the required time points to monitor subject safety during the study.

Vital Signs

At screening the Investigator or designee will obtain vital signs including blood pressure (sitting), pulse, and body weight. Blood pressure (sitting), pulse, and temperature will be on Days 0. Blood pressure (sitting) and pulse will also be measured on Days 7, 14, and 21.

12-Lead Electrocardiograms

At screening the Investigator or designee will obtain an EKG reading. The EKG will again be obtained on Days 0 and 21.

Physical Exam

The Investigator or qualified designee will perform a complete physical exam at the screening visit and on Days 0 and 21. The complete physical exam should include assessment of general appearance, HEENT/Neck, pulmonary system, cardiovascular system, abdomen, extremities, musculoskeletal system, neurological system, and skin.

Clinical Laboratory Results

The following laboratory tests will be obtained at screening and Days 0, 7, 14, and 21. Any clinically significant abnormal laboratory findings will preclude participation in the study.

Blood Chemistry
Alanine Aminotransferase
Aspartate Aminotransferase
Alkaline Phosphatase
Blood Urea Nitrogen
Creatinine
Glucose
Serum Pregnancy Test (βhCG)[1]
HIV antibody[2]
Hepatitis Bs Antigen[2]
Hepatitis C Antibody[2]
Anti-tTG[1]
Hematology
Hemoglobin
Hematocrit
Platelet Count
White Blood Cell Count with Differential
Urinalysis
Protein
Glucose
Ketones
Blood Cells
Leukocyte Esterase
Nitrate
Bilirubin
Urobilinogen
Microscopy
Urine Pregnancy Test (βhCG)[3]
Urine Drug Screen[2]
Amphetamines
Barbituates
Cocaine Metabolites
Opiates
Benzodiazepines
Cannabinoids

[1]Screening and Day 21; [2]Screening; [3]Day 0

Enrollment/Dose Interruption

If any of the following occur, the SPONSOR will interrupt enrollment into the study and drug administration will be halted.

Death in any subject unless clearly UNRELATED to AT-1001 or matching placebo

Anaphylactic reaction to AT-1001 or gluten in any subject

A life-threatening adverse event in any subject unless clearly UNRELATED to AT-1001 or matching placebo Resumption of enrollment and AT-1001 or matching placebo may be determined by the Sponsor after a cumulative review of all available safety data. Written notification to resume enrollment will be provided by the Sponsor.

Subject Discontinuation of Enrollment

If a subject chooses to discontinue the study, an intestinal permeability assay should be done the evening after their last dose of treatment. Subjects should return to the clinic the following day to drop off their intestinal permeability sample. However, subjects should be encouraged to continue with all remaining visits to collect all safety and efficacy endpoints. This includes blood and urine collections throughout the duration of the study, up to Day 21, Visit 5.

If the subject chooses to discontinue the study and all remaining visits prior to Visit 5, the subject should be encouraged to return to the clinic to deliver the intestinal permeability sample and complete all safety and efficacy assessments as outlined for the early termination visit in Table 12.

Emergency Unblinding

If the need arises to unblind a subject's treatment assignment for emergency medical management, the Investigator will contact the Medical Monitor. The Medical Monitor will contact the Sponsor and make a decision on whether to unblind or not. If the decision to unblind is made, written notification will be provided to the Investigator.

Diet and Dosing

Throughout the course of the study, subjects will make every effort to eat three meals per day and remain on a strict gluten free diet. From Day 1 (breakfast) through Day 14 subjects will be administered their treatment regimen. Study drug will be taken orally before breakfast, lunch, and dinner for a total of 14 days. Drug or drug placebo will be ingested 15 minutes prior to each meal and gluten or gluten placebo will be administered during each meal.

To measure intestinal permeability subjects will drink a sugar solution on Day 0 and in the evening prior (Day 6, 13, 20) to their visits on Days 7, 14, and 21. On Day 0 a 6-hour urine will be collected. Subjects will fast for at least 4 hours prior to drinking the sugar solution and NPO (except water) until the end of the 6-hour collection. For the overnight urine collections prior to Days 7, 14, and 21 subjects will have a normal dinner around 6 pm and not eat or drink (except water) until 10 PM. At 10 PM subjects will collect a spot urine sample and void completely, mix the sugar solution according to the instructions contained in the kit (Appendix E), drink the solution, then fast overnight (drinking water is permitted) and collect their overnight and morning urine.

Adverse Events

At the time of informed consent, subjects will be asked to spontaneously report all adverse events that occur during the trial. Additionally subjects will be queried (in a nonspecific manner) about adverse events at each study visit.

Adverse Events will be collected starting at Visit 2 (Day 0) through Visit 5. If a subject discontinues study treatment they will be followed for seven (7) days after last dose.

Definition

An adverse event (AE) can be any unfavorable and unintended sign including an abnormal laboratory finding, symptom, or disease temporally associated with the use of a medicinal product, whether or not considered related to the study drug.

During each visit, the Investigator will question the subject about adverse events using an open question taking care not to influence the subject's answers, e.g. "have you noticed any change in your health?"

When a serious or possibly related adverse event persists at the end of the study, the Investigator will ensure a follow-up of the subject until the Investigator and Sponsor agree the event is satisfactorily resolved.

Severity Rating

The severity of an adverse event is to be scored according to the following scale as set forth in Table 10:

TABLE 10

| | Severity ratings |
| --- | --- |
| Mild | Awareness of sign or symptom, bu easily tolerated |
| Moderate | Discomfort enough to cause interference with usual activity |
| Severe | Incapacitating with inability to work or perform usual activity |

Relationship to Study Drug

The relationship of an adverse event to study treatment is to be assessed according to the following definitions:

Definitely unrelated Should be reserved for those events which occur prior to study treatment or for those events which cannot be even remotely related to study participation (e.g., injuries sustained in an automobile accident).

Unlikely There is no reasonable association between the study treatment and the suspected event and the event could have been produced by the subject's clinical state or other modes of therapy administered to the subject.

Possible The suspected adverse event may or may not follow a reasonable temporal sequence from study treatment administration but seems to be the type of reaction that cannot be dismissed as unlikely. The event could have been produced or mimicked by the subject's clinical state or by other modes of therapy concomitantly administered to the subject.

Probable The suspected adverse event follows a reasonable temporal sequence from study treatment administration, abates upon discontinuation of the treatment, and cannot be reasonably explained by the known characteristics of the subject's clinical state.

Definitely related Should be reserved for those events which have no uncertainty in their relationship to treatment administration.

Expected Side Effects

None related to study drug. Expected gastrointestinal side effects resulting from gluten ingestion include abdominal discomfort, dyspepsia, nausea, diarrhea, vomiting, flatulence or constipation.

Reporting Adverse Events

All clinical events, including either observed or volunteered problems, complaints or symptoms are to be recorded on the Adverse Events page(s) of the case report form (CRF). The need to capture this information is not dependent upon whether the clinical event is associated with study treatment. Adverse clinical events resulting from concurrent illnesses or reactions to concurrent medications are also to be recorded. In order to avoid vague, ambiguous, or colloquial expressions, the adverse event should be recorded in standard medical terminology rather than the subject's own words.

All abdominal discomfort, dyspepsia, nausea, diarrhea, vomiting, flatulence or constipation events comprise the secondary endpoints, measured in the daily and weekly symptom measures, are expected outcomes of the study and will not be collected as adverse events.

Each adverse clinical event is to be evaluated for duration, intensity, and whether the event may be associated with the study drug or other causes. Start and stop dates, relationship to study drug, medical management, and alternative causality of event must be recorded in the Adverse Events section of the CRF. Adverse events believed to be possibly related to study drug must be followed until resolution.

Serious Adverse Events

Definition

A serious adverse event (experience) (SAE) or reaction is defined as any untoward medical occurrence that at any dose:
  results in death
  is life-threatening, (the term "life-threatening" in the definition of "serious" refers to an event in which the subject was at risk of death at the time of the event; it does not refer to an event which hypothetically might have caused death if it were more severe)
  requires in-patient hospitalization or prolongation of existing hospitalization
  results in persistent or significant disability/incapacity
  is a congenital anomaly/birth defect An important medical event that may not result in death, threaten life or require hospitalization may be considered a serious adverse event when, based upon appropriate medical judgment, it may jeopardize the subject and may require medical or surgical intervention to prevent one of the outcomes listed above. Examples of such medical events include allergic bronchospasm requiring intensive treatment in an emergency room or at home, blood dyscrasias or convulsions that do not result in in-patient hospitalization, or the development of drug dependency or drug abuse.

All expected gastrointestinal events (abdominal discomfort, dyspepsia, nausea, diarrhea, vomiting, flatulence or constipation events) which require medical attention, intervention or hospitalization comprise the secondary endpoints measured in the daily and weekly symptom measures, are expected outcomes of the study and will not be collected as serious adverse events.

Reporting

Any SAE, occurring in a subject receiving treatment or if the Investigator becomes aware of any SAE post-treatment, must be reported by the Investigator to the Medical Monitor within 24 hours even if the SAE does not appear to be drug-related. This should be done by telephone and by sending a faxed copy of the Adverse Event form plus other related information. Additionally, it may be necessary for the Sponsor to directly communicate with the Investigator if additional information is required.

All additional follow-up evaluations must be reported to the Medical Monitor. Such data should be sent to the Sponsor within 10 calendar days. All SAEs will be followed until the Investigator and Sponsor agree the event is satisfactorily resolved.

The Sponsor will be responsible for completing the safety report and for notifying the relevant authorities of any SAE as outlined in the ICH Guidelines. The Investigator will also ensure that the appropriate ethics committee is notified of the SAE Clinical Supplies

AT-1001

Drug will be provided to the subject in a white opaque capsule containing approximately 1% AT-1001 enteric coated multi-particulate beads. Capsules will be given with 0.25, 1, 4 or 8 mg of AT-1001.

Drug Placebo

Placebo will be provided to the subject in a white opaque capsule containing enteric coated multi-particulate beads.

Gluten

Orange capsules containing 400 mg gluten, amygluten 160 powder from Tate and Lyle of Decatur, Ill. will be provided. Subjects will take 2 capsules for a dose of 800 mg.

Gluten Placebo

Orange capsules containing 100% corn starch will be provided. Subjects will take 2 capsules.

Lactulose and Mannitol Solution

The sugar solution will consist 5 gm lactulose, 1 gm mannitol, 8 mil glycerin, and water. Great Smokies Diagnostic Laboratory of Asheville, N.C.

Randomization

Enrollment will be centralized to facilitate a balanced, blocked, unstratified randomization. Subjects will be assigned equally to one of the seven study groups. The pharmacist will be responsible for dispensing drug according to the randomization code.

Drug Dispensing

The site pharmacist will receive blinded bottles containing AT-1001, drug placebo, gluten, and gluten placebo. AT-1001 or matching placebo will be labeled with the subject identification number. Dispensation of AT-1001 or matching placebo should be appropriately documented by the pharmacist on the drug accountability form supplied by the Sponsor or its designee.

Method of Administration

All treatments will be administered orally as described in Section 9.0.

Subject Dosing and Treatment Compliance

Subjects will be given treatments to take home with them, along with directions on when and how to take each oral dose.

Drug Accountability

The Investigator or its designee will be responsible for maintaining accurate study drug accountability records and for the security of the drug treatments.

Additional Supplies Provided by Sponsor

The Sponsor will provide the pharmacist with adequate quantities of AT-1001, drug placebo, gluten, and gluten placebo.

Study Conduct

Ethics Committee

This protocol and all appropriate amendments will be properly reviewed and approved by an Ethics Committee. Signed and dated notification of the Ethics Committee approval must be made to the Sponsor and Investigator prior to study initiation. The Investigator will make required progress reports and report Serious Adverse Events (SAEs) to the Ethics Committee.

Ethical Conduct Of The Study

This study will be conducted in accordance with the ethical principles originating from the Declaration of Helsinki and cGCPs and in compliance with local regulatory requirements and 21 CFR 312.

Subject Information And Consent

All subjects in this study are to be completely informed verbally and in writing of the pertinent details and purpose of the study prior to their agreement to participate in the study in accordance to cGCPs and local regulatory authority requirements. A written consent form, approved by an Ethics Committee, will be supplied by the Investigator and will be understood and signed by each subject prior to dispensing test materials. The Investigator is responsible for maintaining each subject's consent form in the study file and providing each subject with a signed copy of the consent form.

The requirements of an informed consent are included in Appendix F.

Protocol Adherence

The Investigator must read the protocol thoroughly and must follow the instructions exactly. Any deviations should be agreed to by prior discussion between the Sponsor and the Investigator, with appropriate written protocol amendments made prior to effecting the changes agreed upon. Any amendment containing major modifications (particularly if it may involve an increased risk to the subjects) will be approved by the Ethics Committee before it may be implemented.

Contractual Requirements

Contractual agreements will be signed between the Sponsor and the Investigator. These documents will contain complementary information, i.e., financial agreement, confidentiality, study schedule, third party responsibility, and publication of study results.

Record Keeping

Data Collection

The Investigator must maintain detailed records on all study subjects. Data for this study will be recorded in the subject's chart, in electronic files, and on CRFs provided by the Sponsor or its designee. Data on the CRFs should be recorded completely, promptly, and legibly using black ink. Original source documents (paper and electronic) and other study documentation will be maintained at the study site as specified. Upon study completion or at any other time specified by the site monitor, the appropriate CRF pages will be collected.

The original CRF will be archived by the Sponsor after study completion. A copy will be archived at the Investigator site.

Data Corrections

Completed CRFs, and electronic records should be ready for inspection within three (3) weeks after the End of Study visit for a given subject unless data is pending for that subject due to laboratory data or adverse event follow-up that is not yet available.

The sponsor will review the CRFs, and electronic source/CRF data, evaluate them for completeness and accuracy, and ensure all appropriate corrections are made.

Any changes made to the CRF or the electronic source/CRF data after the last monitoring visit will be discussed with and approved by the Investigator.

Source Documentation

Investigator must keep accurate separate records (other than the CRFs) of all subjects' visits, being sure to include all pertinent study related information. Any and all side effects and adverse events must be thoroughly documented. Results of any diagnostic tests conducted during the study should also be included in the source documentation. Telephone conversations with the subjects and/or Sponsor concerning the study must also be documented.

Case Report Forms

Case report forms will be provided for each subject receiving AT-1001 or matching placebo.

Monitoring

The Sponsor or its designee will be responsible for monitoring the study, data entry and data management.

A pre-study/initiation visit will be conducted with the Principal Investigator and Study Coordinator(s), if any. During this meeting, an extensive review and discussion of the protocol, procedures, and CRFs will be conducted.

The conduct of the study will be closely monitored by the Sponsor and/or its designee following GCP guidelines. The reports of these verifications will also be archived with the study report. The Investigator will allow the Sponsor's representatives, its designees, and any regulatory agency to examine all study records, CRFs, corresponding subject medical records, clinical drug dispensing records and drug storage area, and any other documents considered source documentation. The Investigator also agrees to assist the representative, if required.

Record Retention

All CRFs and pertinent data, correspondence, original or amended protocol, all reports and all other material relating to the study will be maintained securely in the Investigator's files indefinitely.

Statistical Methods

This study is a multi-center, randomized, placebo controlled study.

Subjects will be considered protocol valid if they received study medication and completed all study evaluations without noteworthy study protocol violations (i.e., any subject or investigator activity that could have possibly interfered with the therapeutic administration of the treatment or the precise evaluation of treatment safety). The decision to exclude a patient from the per-protocol sample will be made prior to unblinding the data.

The efficacy analysis will consider only the five treatment groups that receive gluten. The analysis will be focused on identifying the active dose or doses that are statistically different from the placebo dose. The null hypothesis for efficacy is that there is no difference between the placebo and any active treatment. A two-sided alpha of .05 will be used. The safety analysis will consider all seven treatment groups. The null hypothesis for safety is that there is no difference among the treatment groups. A two-sided critical significance level of 0.05 will be used throughout. Except where otherwise stated, no corrections for multiple comparisons will be performed. The assumptions underlying all statistical methods will be assessed prior to accepting the results. Each efficacy analysis will be performed for the ITT group and optionally for the per-protocol group.

Complete details of the statistical analysis will be given in a separate statistical analysis plan to be finalized prior to unblinding the study.

Analyses will be performed in SAS/STAT statistical software, version 8.2 or later.

Missing values will not be imputed in the primary efficacy analysis. But, if any study arm has 3 or more of 11 values (or 13 for the placebo arm) that are missing for the L-to-M ratio on either Day 0 or Day 14, a sensitivity analysis will create samples with all missing L-to-M ratios set to their $10^{th}$ percentile or all set to their $90^{th}$ percentile.

Efficacy Analysis

Efficacy Measurements:

A subject's measurement of intestinal permeability (IP) at Day x is divided by his or her IP at Day 0. The result, a fold-ratio, expresses a subject's response to treatment and gluten challenge. Values are transformed to the log base-10 scale prior to statistical analysis. Treatment group differences on the log scale become treatment group ratios on the original scale. The fold-ratio for Day 0, by definition, as a value of 1. Treatment group results are expressed as geometric means. The ratio of geometric means between two treatment groups expresses their relative efficacy.

Analysis of the Primary Outcome

The primary efficacy outcome is change in fold-ratio between Day 0 and a subject's last day of gluten challenge (usually Day 14). The outcome will be evaluated with analysis of variance, in a model containing only a fixed effect for treatment. Adjusted (least squares) means for each treatment group will be calculated with the 95% confidence interval. Each active treatment will then be compared with the placebo treatment, using a standard correction for multiple comparisons. Adjusted estimates, 95% confidence intervals, and adjusted p-values for the difference between each active group and placebo will be obtained. A two-sided alpha of 0.05 will be used.

Secondary, Exploratory Analyses:

Several continuous secondary efficacy outcomes are collected These outcomes are L-to-M ratios at other time points, urinary fractional excretion of lactulose and mannitol, nitrate/nitrite excretion, anti-tTG levels, cell markers and cytokines from PBMCs, and zonulin levels. Their analyses are handled in the same way as the primary outcome. Subject daily and weekly health outcomes will be described by mean and standard deviation.

A further exploratory analysis will concern the day of dropout in each of the four study arms. Those not dropping out before Day 14 are censored at that time. Results will compare each AT-1001 dosage group to the placebo group. The preferred study group is the one with the fewest and latest dropouts.

Safety Analysis
Safety and Tolerance Parameters:
Monitoring of adverse events (AEs)
Clinical laboratory testing of blood and urine including standard safety panels for chemistry, hematology, and urinalysis
Vital signs
Physical exam results
EKG
AT-1001 plasma levels
Analysis of Safety Variables All subjects who receive treatment and have a subsequent safety evaluation will be included in the safety analyses. All adverse events reported during the study will be listed, documenting course, severity, and outcome.

Adverse events reports summarized by treatment will give the number of subjects who experienced an adverse event, the maximum severity, and body system.

Laboratory parameters, vital signs, physical exam and AT-1001 levels results will be summarized with the statistics of n, mean, standard deviation, median and range or frequencies and percentages, as appropriate.

EKG results will be classified as normal, abnormal, not clinically significant and abnormal clinically significant.

Sample Size and Power Considerations

A subject's measurement of intestinal permeability (IP) at Day 14 is divided by his or her IP at Day 0. The result, a fold-ratio, expresses a subject's response to treatment and gluten challenge. Treatment group results are expressed as geometric means. The ratio of geometric means between two treatment groups expresses their relative efficacy. Upon log-transformation, the expression of relative efficacy becomes a difference of logarithms. This fact allows the use of standard sample size calculation methods, which focus on the difference between groups.

A clinically important effect size for this outcome is a 3-fold reduction in IP between any test dose and placebo. Sample size calculation was based on a t-test for differences between two groups, using NQuery Advisor 4.0. The standard deviation for log-transformed fold-ratios was taken as 0.3 based on earlier trials conducted by the Sponsor. It was found that 8 patients per group would be sufficient to have good power (80%) of demonstrating a statistically significant difference (less than 0.05) between groups. A final sample size of 11 subjects per test group allows up to three dropouts; the sample size of 13 subjects in the placebo group allows up to five dropouts.

TABLE 12

STUDY PROCEDURES

| Procedure | Visit 1 Screen | Visit 2 Day 0 | Visit 3 Day 7 | Visit 4 Day 14 | Visit 5 Day 21 | Early Termination |
|---|---|---|---|---|---|---|
| Consent | X | | | | | |
| Inclusion/Exclusion Criteria | X | X | | | | |
| Randomize subject | | X | | | | |
| Medical History | X | | | | | |
| Physical Exam | X | X | | | X | X |
| Vital Signs | X | X | X | X | X | X |
| EKG | X | X | | | X | X |
| HIV, Hepatitis B and Hepatitis C | X | | | | | |
| Serum βhCG (all females) | X | | | | X | X |
| Urine βhCG (all females) | | X | | | | |
| Chemistry, Hematology, Urinalysis | X | X | X | X | X | X |
| Urine Drug Screen | X | | | | | |
| Serum anti-tTG | X | | | | X | X |
| Dispense Study Drug | | X | | | | |
| Administer IP kit in clinic | | X | | | | |
| Provide IP kit to Subject | | | X | X | X | |
| Process Overnight Urine | | | X | X | X | X |
| Nitrite/Nitrate Spot Urine | | X | | X | | X |
| Plasma Sample (AT-1001) | | X | X | X | | X |
| PBMC Sample | | X | X | X | X | X |
| Zonulin Sample | | X | | X | X | X |
| Monitor Concurrent Medications | Collected throughout the study | | | | | |
| Monitor for Adverse Events | Collected throughout the study | | | | | |
| Administer Weekly Health and GI | | X | X | X | X | X |

TABLE 13

SUMMARY OF BLOOD DRAW VOLUMES (mL)

| Procedure | Visit 1 Screen | Visit 2 Day 0 | Visit 3 Day 7 | Visit 4 Day 14 | Visit 5 Day 21 |
|---|---|---|---|---|---|
| HIV, Hepatitis Bs antigen and Hepatitis C | 2.5 | | | | |
| Serum βhCG (all females) | X | | | | X |
| Chemistry, Hematology | 10 | 10 | 10 | 10 | 10 |
| Serum anti-tTG | 2.5 | | | | 2.5 |
| Plasma Sample (AT-1001) | | 3 | 3 | 3 | |
| PBMC Sample | | 25 | 20 | 20 | 20 |
| Zonulin Sample | | 3 | | 3 | 3 |
| Per Visit Blood Volume | 15 | 41 | 33 | 36 | 38.5 |
| Cumulative Study Blood Volume | | | 163.5 | | |
| X included in chemistry volume | | | | | |

APPENDIX C: SUBJECT'S REPORTED SYMPTOMS (DAILY BOWEL DIARY)

This survey contains questions about how you have been feeling about your gastrointestinal symptoms and what it has been like DURING THE ENTIRE DAY. Select the choice that best applies to you and your situation.

Gastrointestinal Symptoms

Have you felt or experienced a sense of urgency today?    Yes___ No___

How many bowel movements did you have today?    ____

How many episodes of diarrhea did you have today? ____

Please rate your average stool consistency today

1 = watery

2 = loose

3 = somewhat loose

4 = neither loose nor hard

5 = somewhat hard

6 = hard

7 = very hard

How intense was your abdominal discomfort and pain today?

1 = none

2 = very mild

3 = mild

4 = moderate

5 = moderate severe

6 = severe

7 = very severe

APPENDIX D: SUBJECT'S REPORTED HEALTH OUTCOMES (WEEKLY)

THE GENERAL WELL-BEING SCHEDULE

NAME: _____ SEX: M: [ ] F: [ ] AGE:___
      Last      First      Middle

*READ: This section of the examination contains questions about how you feel and how things have been going with you. For each question check [ ] the answer which best applies to you.*

1. How have you been feeling in general during the past week?
(Check one box)
- In excellent spirits ☐
- In very good spirits ☐
- In good spirits mostly ☐
- I have been up and down in spirits a lot ☐
- In low spirits mostly ☐
- In very low spirits ☐

2. How often were you bothered by any illness, bodily disorder, aches or pains during the past week?
(Check one box)
- Every day ☐
- Almost every day ☐
- About half of the time ☐
- Now and then, but less than half the time ☐
- Rarely ☐
- None of the time ☐

3. Did you feel depressed during the past week?
(Check one box)
- Yes - to the point that I felt like taking my life ☐
- Yes - to the point that I did not care about anything ☐
- Yes - very depressed almost every day ☐
- Yes - quite depressed several times ☐
- Yes - a little depressed now and then ☐
- No - never felt depressed at all ☐

4. Have you been in firm control of your behavior, thoughts, emotions or feelings during the past week?
(Check one box)
- Yes, definitely so ☐
- Yes, for the most part ☐
- Generally so ☐
- Not too well ☐
- No, and I am somewhat disturbed ☐
- No, and I am very disturbed ☐

5. Have you been bothered by nervousness or your "nerves" during the past week?
(Check one box)

Extremely so - to the point where I could not work or take care of things ...... ☐

Very much so ................................................................................................ ☐

Quite a bit .................................................................................................... ☐

Some - enough to bother me ........................................................................ ☐

A little .......................................................................................................... ☐

Not at all ...................................................................................................... ☐

6. How much energy, pep, or vitality did you have or feel during the past week?
(Check one box)

Very full of energy - lots of pep .................................................................. ☐

Fairly energetic most of the time ................................................................ ☐

My energy level varied quite a bit .............................................................. ☐

Generally low in energy or pep .................................................................. ☐

Very low in energy or pep most of the time .............................................. ☐

No energy or pep at all - I felt drained, sapped ........................................ ☐

7. I felt downhearted and blue during the past week.
(Check one box)

None of the time .......................................................................................... ☐

A little of the time ...................................................................................... ☐

Some of the time .......................................................................................... ☐

A good bit of the time ................................................................................ ☐

Most of the time .......................................................................................... ☐

All of the time ............................................................................................ ☐

8. Were you generally tense or did you feel any tension during the past week?
(Check one box)

Yes - extremely tense, most or all of the time .......................................... ☐

Yes - very tense most of the time .............................................................. ☐

Not generally tense, but did feel fairly tense several times ...................... ☐

I felt a little tense a few times .................................................................. ☐

My general tension level was quite low .................................................... ☐

I never felt tense or any tension at all ...................................................... ☐

9. How happy, satisfied, or pleased have you been with your personal life during the past week?
(Check one box)

Extremely happy - could not have been more satisfied or pleased .................. ☐

Very happy most of the time ...................................................................... ☐

Generally satisfied - pleased ...................................................................... ☐

Sometimes fairly happy, sometimes fairly unhappy .................................. ☐

Generally dissatisfied or unhappy .............................................................. ☐

Very dissatisfied or unhappy most or all the time .................................... ☐

10. Did you feel healthy enough to carry out the things you like to do or had to do during the past week?
    (Check one box)
    Yes - definitely so .................................................................................... ☐
    For the most part ....................................................................................... ☐
    Health problems limited me in some important ways ........................... ☐
    I was only healthy enough to take care of myself ................................. ☐
    I needed some help in taking care of myself ........................................ ☐
    I needed someone to help me with most or all of the things I had to do .......... ☐

11. Have you felt so sad, discouraged, hopeless, or had so many problems that you wondered if anything was worthwhile during the past week?
    (Check one box)
    Extremely so - to the point that I have just about given up ................. ☐
    Very much so ............................................................................................ ☐
    Quite a bit ................................................................................................. ☐
    Some - enough to bother me .................................................................. ☐
    A little bit ................................................................................................. ☐
    Not at all ................................................................................................... ☐

12. I woke up feeling fresh and rested during the past week.
    (Check one box)
    None of the time ...................................................................................... ☐
    A little of the time ................................................................................... ☐
    Some of the time ...................................................................................... ☐
    A good bit of the time ............................................................................. ☐
    Most of the time ....................................................................................... ☐
    All of the time .......................................................................................... ☐

13. Have you been concerned, worried, or had any fears about your health during the past week?
    (Check one box)
    Extremely so ............................................................................................. ☐
    Very much so ............................................................................................ ☐
    Quite a bit ................................................................................................. ☐
    Some, but not a lot ................................................................................... ☐
    Practically never ....................................................................................... ☐
    Not at all ................................................................................................... ☐

14. Have you had any reason to wonder if you were losing your mind, or losing control over the way you act, talk, think, feel or of your memory during the past week?
    (Check one box)
    Not at all ................................................................................................... ☐
    Only a little ............................................................................................... ☐
    Some - but not enough to be concerned or worried about ................... ☐
    Some and I have been a little concerned ............................................... ☐
    Some and I am quite concerned .............................................................. ☐
    Yes, very much so and I am very concerned ......................................... ☐

15. My daily life was full of things that were interesting to me during the past week.
  Check one box)
  None of the time ................................................................................................. ☐
  A little of the time ............................................................................................... ☐
  Some of the time ................................................................................................. ☐
  A good bit of the time ......................................................................................... ☐
  Most of the time .................................................................................................. ☐
  All of the time ..................................................................................................... ☐

16. Did you feel active, vigorous, or dull, sluggish during the past week?
  (Check one box)
  Very active, vigorous every day ......................................................................... ☐
  Mostly active, vigorous - never really dull, sluggish ......................................... ☐
  Fairly active, vigorous - seldom dull, sluggish .................................................. ☐
  Fairly dull, sluggish - seldom active, vigorous .................................................. ☐
  Mostly dull, sluggish - never really active, vigorous ......................................... ☐
  Very dull, sluggish every day ............................................................................. ☐

17. Have you been anxious, worried, or upset during the past week?
  (Check one box)
  Extremely so - to the point of being sick or almost sick ................................... ☐
  Very much so ...................................................................................................... ☐
  Quite a bit ........................................................................................................... ☐
  Some - enough to bother me .............................................................................. ☐
  A little bit ........................................................................................................... ☐
  Not at all ............................................................................................................. ☐

18. I was emotionally stable and sure of myself during the past week.
  (Check one box)
  None of the time ................................................................................................. ☐
  A little of the time ............................................................................................... ☐
  Some of the time ................................................................................................. ☐
  A good bit of the time ......................................................................................... ☐
  Most of the time .................................................................................................. ☐
  All of the time ..................................................................................................... ☐

19. Did you feel relaxed, at ease or high strung, tight, or keyed-up during the past week?
  (Check one box)
  Felt relaxed and at ease the whole week ............................................................ ☐
  Felt relaxed and at ease most of the time ........................................................... ☐
  Generally felt relaxed but at times felt fairly high strung ................................. ☐
  Generally felt high strung but at times felt fairly relaxed ................................. ☐
  Felt high strung, tight, or keyed-up most of the time ........................................ ☐
  Felt high strung, tight, or keyed-up the whole week ......................................... ☐

20. I felt cheerful, lighthearted during the past week.
    (Check one box)
    None of the time .................................................................................... ☐
    A little of the time ................................................................................. ☐
    Some of the time ................................................................................... ☐
    A good bit of the time ........................................................................... ☐
    Most of the time .................................................................................... ☐
    All of the time ....................................................................................... ☐

21. I felt tired, worn out, used up, or exhausted during the past week.
    (Check one box)
    None of the time .................................................................................... ☐
    A little of the time ................................................................................. ☐
    Some of the time ................................................................................... ☐
    A good bit of the time ........................................................................... ☐
    Most of the time .................................................................................... ☐
    All of the time ....................................................................................... ☐

22. Have you been under or felt you were under any strain, stress, or pressure during the past week?
    (Check one box)
    Yes - almost more than I could bear or stand ...................................... ☐
    Yes - quite a bit of pressure .................................................................. ☐
    Yes, some - more than usual ................................................................. ☐
    Yes, some - but about usual .................................................................. ☐
    Yes - a little .......................................................................................... ☐
    Not at all ............................................................................................... ☐

APPENDIX E: The Gastrointestinal Symptom Rating Scale

THE GASTROINTESTINAL SYMPTOM RATING SCALE
(GSRS)

---

Please read this first:

This survey contains questions about how you have been feeling and what it has been like DURING THE PAST WEEK. Mark the choice that best applies to you and your situation with an "X" in the box.

---

1. Have you been bothered by PAIN OR DISCOMFORT IN YOUR UPPER ABDOMEN OR THE PIT OF YOUR STOMACH during the past week?

☐ No discomfort at all
   ☐ Minor discomfort
   ☐ Mild discomfort
   ☐ Moderate discomfort
   ☐ Moderately severe discomfort
   ☐ Severe discomfort
   ☐ Very severe discomfort 2. Have you been bothered by HEARTBURN during the past week? (By heartburn we mean an unpleasant stinging or burning sensation in the chest.)

☐ No discomfort at all
   ☐ Minor discomfort
   ☐ Mild discomfort
   ☐ Moderate discomfort
   ☐ Moderately severe discomfort
   ☐ Severe discomfort
   ☐ Very severe discomfort 3. Have you been bothered by ACID REFLUX during the past week? (By acid reflux we mean the sensation of regurgitating small quantities of acid or flow of sour or bitter fluid from the stomach up to the throat.)

☐ No discomfort at all
   ☐ Minor discomfort
   ☐ Mild discomfort
   ☐ Moderate discomfort
   ☐ Moderately severe discomfort
   ☐ Severe discomfort
   ☐ Very severe discomfort 4. Have you been bothered by HUNGER PAINS in the stomach during the past week? (This hollow feeling in the stomach is associated with the need to eat between meals.)

☐ No discomfort at all
   ☐ Minor discomfort
   ☐ Mild discomfort
   ☐ Moderate discomfort
   ☐ Moderately severe discomfort
   ☐ Severe discomfort
   ☐ Very severe discomfort 5. Have you been bothered by NAUSEA during the past week? (By nausea we mean a feeling of wanting to throw up or vomit.)

☐    No discomfort at all
    ☐    Minor discomfort
    ☐    Mild discomfort
    ☐    Moderate discomfort
    ☐    Moderately severe discomfort
    ☐    Severe discomfort
    ☐    Very severe discomfort 6. Have you been bothered by RUMBLING in your stomach during the past week? (Rumbling refers to vibrations or noise in the stomach.)

☐    No discomfort at all
    ☐    Minor discomfort
    ☐    Mild discomfort
    ☐    Moderate discomfort
    ☐    Moderately severe discomfort
    ☐    Severe discomfort
    ☐    Very severe discomfort 7. Has your stomach felt BLOATED during the past week? (Feeling bloated refers to swelling often associated with a sensation of gas or air in the stomach.)

☐    No discomfort at all
    ☐    Minor discomfort
    ☐    Mild discomfort
    ☐    Moderate discomfort
    ☐    Moderately severe discomfort
    ☐    Severe discomfort
    ☐    Very severe discomfort 8. Have you been bothered by BURPING during the past week? (Burping refers to bringing up air or gas from the stomach via the mouth, often associated with easing a bloated feeling.)

☐    No discomfort at all
    ☐    Minor discomfort
    ☐    Mild discomfort
    ☐    Moderate discomfort
    ☐    Moderately severe discomfort
    ☐    Severe discomfort
    ☐    Very severe discomfort 9. Have you been bothered by PASSING GAS OR FLATUS during the past week? (Passing gas or flatus refers to the need to release air or gas from the bowel, often associated with easing a bloated feeling.)

☐    No discomfort at all
    ☐    Minor discomfort
    ☐    Mild discomfort
    ☐    Moderate discomfort
    ☐    Moderately severe discomfort
    ☐    Severe discomfort
    ☐    Very severe discomfort 10. Have you been bothered by CONSTIPATION during the past week? (Constipation refers to a reduced ability to empty the bowels.)

☐ No discomfort at all
    ☐ Minor discomfort
    ☐ Mild discomfort
    ☐ Moderate discomfort
    ☐ Moderately severe discomfort
    ☐ Severe discomfort
    ☐ Very severe discomfort 11. Have you been bothered by DIARRHEA during the past week? (Diarrhea refers to a too frequent emptying of the bowels.)

☐ No discomfort at all
    ☐ Minor discomfort
    ☐ Mild discomfort
    ☐ Moderate discomfort
    ☐ Moderately severe discomfort
    ☐ Severe discomfort
    ☐ Very severe discomfort 12. Have you been bothered by LOOSE STOOLS during the past week? (If your stools (motions) have been alternately hard and loose, this question only refers to the extent you have been bothered by the stools being loose.)

☐ No discomfort at all
    ☐ Minor discomfort
    ☐ Mild discomfort
    ☐ Moderate discomfort
    ☐ Moderately severe discomfort
    ☐ Severe discomfort
    ☐ Very severe discomfort 13. Have you been bothered by HARD STOOLS during the past week? (If your stools (motions) have been alternately hard and loose, this question only refers to the extent you have been bothered by the stools being hard.)

☐ No discomfort at all
    ☐ Minor discomfort
    ☐ Mild discomfort
    ☐ Moderate discomfort
    ☐ Moderately severe discomfort
    ☐ Severe discomfort
    ☐ Very severe discomfort 14. Have you been bothered by an URGENT NEED TO HAVE A BOWEL MOVEMENT during the past week? (This urgent need to go to the toilet is often associated with a feeling that you are not in full control.)

☐ No discomfort at all
    ☐ Minor discomfort
    ☐ Mild discomfort
    ☐ Moderate discomfort
    ☐ Moderately severe discomfort
    ☐ Severe discomfort
    ☐ Very severe discomfort 15. When going to the toilet during the past week, have you had the SENSATION OF NOT COMPLETELY EMPTYING THE BOWELS? (This feeling of incomplete emptying means that you still feel a need to pass more stool despite having exerted yourself to do so.)

- ☐ No discomfort at all
- ☐ Minor discomfort
- ☐ Mild discomfort
- ☐ Moderate discomfort
- ☐ Moderately severe discomfort
- ☐ Severe discomfort
- ☐ Very severe discomfort

PLEASE CHECK THAT ALL QUESTIONS HAVE BEEN ANSWERED!

THANK YOU FOR YOUR CO-OPERATION.

Example 3

In Vivo Measurement of Intestinal Permeability

Selection of region specific probes allows for the determination of paracellular permeability in different segments (Arrieta et al. Gut. 55; pp1512-1520 (2006)).

Lactulose:Mannitol (La/Ma) ratios provide information on the entire small bowel

LactuloseFE~pore injury
MannitolFE~absorptive surface area
La/Ma=injury/unit area Subject Instructions for Intestinal Permeability Test This is a safe, simple urine test designed to study changes in bowel permeability (leakiness), which may help us predict inflammation in the bowels.

Please follow the instructions carefully.

The test kit contains
One bottle for urine collection
One bottle of mannitol/lactulose syrup
One collection "hat" to help you collect urine
Steps to follow:
Do not drink alcohol for 2 days before performing the test.
On the day before your scheduled study visit, take your study drug as directed and have a normal supper (around 6 pm). After supper do not eat or drink until 10 pm.
At 10 pm, empty your bladder.
At 10 pm, fill the bottle of lactulose/mannitol with water up to the "fill line". Replace lid and mix drink by shaking vigorously. Drink all of the solution.
Rinse with a small amount of water twice to ensure you drink all the sugars.
Fast overnight. You may consume as much water as you like but NO other liquid or foods.
Prior to bedtime, place the "hat" over the toilet and collect your first urine sample. Store this urine in the urine collection bottle that we have provided. If you have to get up at night to pass urine, that's OK, just remember to also collect ALL of your urine through the night in the "hat" and pour it into the urine collection bottle after each void. Remember to collect the first urine you pass in the morning as well. Do not pass urine directly into the collecting bottle.
Keep the bottle refrigerated inside a plastic bag (do not worry, the urine will not leak). Bring your bottle to your doctor's office first thing in the morning. Please keep the bottle refrigerated until you bring it to the doctor's office.

Example 4

Basic Elements of Informed Consent

The following information must be provided to each subject in obtaining informed consent. The subject (or subject's legal representative) should be provided with a copy of the signed written informed consent.

1. State that the study involves RESEARCH.
   a. Explain the PURPOSES of the research.
   b. State the expected DURATION of the subject's participation.
   c. Describe the PROCEDURES to be followed.
   d. Identify any EXPERIMENTAL procedures.
2. Describe any reasonably foreseeable RISKS OR DISCOMFORTS to the subject.
3. Describe any BENEFITS to the subject or to others which may reasonably be expected from the research.
4. Note appropriate ALTERNATIVE procedures or courses of treatment, if any, that might be advantageous to the subject.
5. a. Describe the extent, if any, to which CONFIDENTIALITY of records identifying the subject will be maintained.
   b. Note that the Food and Drug Administration MAY INSPECT the records.
6. For research involving more than minimal risk, explain if any COMPENSATION or medical treatments are available should injury occur. If so, explain (a) what they consist of, OR (b) where further information may be obtained.
7. Tell who to contact for ANSWERS to pertinent questions about (a) the research, and (b) research subject's rights.
8. State that:
   a. participation is VOLUNTARY,
   b. refusal to participate will involve NO PENALTY or loss of benefits to which the subject is otherwise entitled, and
   c. the subject MAY DISCONTINUE participation at any time without penalty or loss of benefits to which the subject is otherwise entitled.

Additional Elements of Informed Consent

When appropriate, one or more of the following elements of information shall also be provided to each subject:

1. A statement that the particular treatment or procedure may involve risks to the subject (or to the embryo or fetus, if the subject is or may become pregnant) which are currently unforeseeable.
3. Any additional costs to the subject that may result from participation in the research.
4. The consequences of a subject's decision to withdraw from the research and procedures for orderly termination of participation by the subject.
5. A statement that significant new findings developed during the course of the research which may relate to the subject's willingness to continue participation will be provided to the subject.
6. The approximate number of subjects involved in the study.

Reference: 21 CRF Part 50.25

Protection of Human Subjects, Basic Elements of Informed Consent

The informed consent requirements in these regulations are not intended to preempt any applicable federal, state, or local laws which require additional information to be disclosed for informed consent to be legally effective.

Example 5

AT-1001 Drug Substance

AT-1001 is an octapeptide, acetate salt
Competitive human zonulin receptor antagonist
Stored as white lyophilized powder at −70° C.
Solubility is greater than 1 mg/ml in many aqueous and organic solvents
Stable up to 1 year at room temperature

Example 6

Clinical Trial Summary—AT-1001 in Celiac Disease

CLIN1001-001a—Single Dose Safety Study (Phase I)
First Human Dose
Completed, October 2005
CLIN1001-002—Single-Dose, Proof of Concept (Phase Ib POC)

Celiac Disease
  Completed, March 2006
CLIN1001-003—Multi-Dose Safety Study (Phase I)
  Healthy Volunteers
  Completed, April 2006
CLIN1001-004—Multi-Dose Proof of Concept (Phase II)
  Celiac Disease
  First patient dosed September 2006, currently recruiting patients
Results Summary—Single Dose Safety Study—CLIN1001-001
  3 cohorts dosed at three escalating doses of AT-1001 or placebo (24 healthy subjects)
  No Serious Adverse Events (SAEs)
  Adverse Events (AEs) were mild or moderate in severity
  Headache was the most common AE
  No Clinically Significant trends related to safety
  No measurable plasma drug levels (11q=0.5 ng/ml)
Results Summary—Multiple Dose Safety Study—CLIN1001-003
  3 dose level cohorts dosed with AT-1001 or placebo 3 times a day for 10 days (24 healthy subjects)
  No Serious Adverse Events (SAEs)
  Adverse Events (AEs) were all mild in severity
  Headache was the most common AE
  No measurable plasma drug levels (11q=0.5 ng/ml)
  Phase Ib Proof Of Concept Trial Endpoints
Primary Endpoint:
  Intestinal Permeability (La/Ma)—day 2 v. day 1
Investigational Endpoints:
  Other La/Ma comparisons
  Cytokines (INF-γ, TNF-α, IP-10, IL-6, etc.)
  Surface Markers (CD40, HLA-DR, etc.)
  Urinary Nitrate/Nitrite (iNOS)
  Gluten associated adverse events
  Patient symptom scores and outcome measure
  AT-1001 Plasma Levels
  Phase Ib Proof Of Concept Trial Efficacy Conclusions
Intestinal Permeability:
  Intestinal barrier function during a supramaximal stimulus (2.5 gm gluten challenge) is maintained by 12 mg AT-1001
Celiac Symptoms:
  Symptoms of acute gluten toxicity inhibited, and yet placebo effect of close inpatient setting likely biased against drug effect
Biological effect persists far beyond drug effect:
  Suggests AT-1001 EC formulation blocks persistent leak and immune activation
  PBMC Derived Cytokines, AT1001 versus placebo:
    Trend to Reduction in INF-γ TNF-γ may suggest mitigation of cell mediated immunity
  Cell Markers, AT1001 versus placebo:
    HLA-DR other markers trends favor drug arm
  iNOS Induction, AT1001 versus placebo:
    Urinary Nitrates Suggest inhibition of iNOS induction by gluten challenge Interpreting Lactulose:Mannitol data
Mannitol Clearance:
  proportional to mature, villus tip surface area
Lactulose Clearance:
  "Damage"—more 'large holes' that are now accessible by lactulose
Lactulose/Mannitol Ratio:
  Damage per unit surface area
Study Objectives—Multiple Dose POC Study—CLIN1001-004 (Phase IIa)
  To demonstrate the safety and tolerability of multiple, oral doses of AT-1001 in celiac disease subjects "in remission" [anti-tTG (−)≤10 EU]
  To evaluate the efficacy of multiple dose levels of EC AT-1001 in preventing intestinal permeability changes induced by gluten
    Change in urinary lactulose-to-mannitol (La/Ma) ratio from Day 0 to Day 14; a measure of intestinal permeability in response to gluten exposure
    A sub-chronic measure of injury/unit area vs. the acute drug exposure effect measured in Phase Ib
  To evaluate the effects of multiple dose levels of EC AT-1001 in preventing the induction of celiac disease signs and symptoms resulting from gluten challenge
Study Hypothesis—Multiple Dose POC Study—CLIN1001-004 (Phase IIa)
  Placebo/gluten challenge different from placebo/placebo
  Each drug/gluten arm different from placebo/gluten
  AT-1001/placebo not different from placebo/placebo
(Intestinal Permeability Endpoint: Day X vs Baseline)

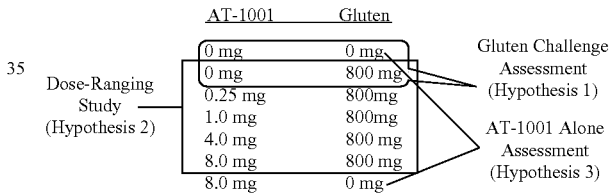

Primary comparison for all subjects is a ratio of Day 14 to their baseline, Day 0 (Day 14: Day 0)
Patient Population—Multiple Dose POC Study—CLIN1001-004 (Phase IIa)
  Open to biopsy diagnosed celiacs between 18 and 65 years of age who have been observing a gluten free diet for longer than 6 months, and whose anti-tTG levels are less than 10 EU.
  Intent to Treat—all randomized subjects, 86
  Per Protocol—excludes subjects who violated protocol criteria or did not complete study, 74
  Early Terminations—6
    4 due to gluten toxicity vs. 8 predicted

TABLE 14

Patient Demographics - Multiple dose POC study - CLIN1001-004 (Phase IIa)

| | Control Arms | | | AT-1001 Treated, Gluten Challenge Arms | | | | |
|---|---|---|---|---|---|---|---|---|
| | P/G (n = 14) | P/P (n = 12) | 8 mg/P (n = 12) | 0.25 mg (n = 12) | 1 mg (n = 12) | 4 mg (n = 12) | 8 mg (n = 12) | Total (n = 86) |
| Age (yrs) | | | | | | | | |
| n | 14 | 12 | 12 | 12 | 12 | 12 | 12 | 86 |
| Mean | 41.5 | 46.7 | 44.4 | 50.4 | 44.9 | 50.5 | 46.3 | 46.3 |
| S.D. | 13.54 | 12.94 | 9.82 | 6.65 | 13.24 | 14.25 | 9 | 11.7 |
| Median | 46.5 | 47 | 45 | 50.5 | 45 | 53 | 46 | 47 |

TABLE 14-continued

Patient Demographics - Multiple dose POC study - CLIN1001-004 (Phase IIa)

| | Control Arms | | | AT-1001 Treated, Gluten Challenge Arms | | | | |
|---|---|---|---|---|---|---|---|---|
| | P/G (n = 14) | P/P (n = 12) | 8 mg/P (n = 12) | 0.25 mg (n = 12) | 1 mg (n = 12) | 4 mg (n = 12) | 8 mg (n = 12) | Total (n = 86) |
| Minimum | 19 | 24 | 29 | 39 | 21 | 26 | 34 | 19 |
| Maximum | 59 | 65 | 64 | 64 | 62 | 66 | 65 | 66 |
| Sex | | | | | | | | |
| Male | 4 | 3 | 5 | 7 | 4 | 4 | 3 | 30 |
|  | 28.6% | 25.0% | 41.7% | 58.3% | 33.3% | 33.3% | 25.0% | 34.9% |
| Female | 10 | 9 | 7 | 5 | 8 | 8 | 9 | 56 |
|  | 71.4% | 75.0% | 58.3% | 41.7% | 66.7% | 66.7% | 75.0% | 65.1% |
| Race | | | | | | | | |
| Caucasian | 14 | 12 | 12 | 12 | 11 | 12 | 12 | 85 |
|  | 100.0% | 100.0% | 100.0% | 100.0% | 91.7% | 100.0% | 100.0% | 98.8% |
| Other | 0 | 0 | 0 | 0 | 1 | 0 | 0 | 1 |
|  | 0.0% | 0.0% | 0.0% | 0.0% | 8.3% | 0.0% | 0.0% | 1.2% |

Preliminary Observations—Multiple Dose POC Study—CLIN1001-004 (Phase IIa)

Safety and tolerability of multiple oral doses of AT-1001 in patient population was demonstrated:

No Serious Adverse Events (SAEs)

Adverse Events (AEs) were mild or moderate in severity

Headache was the most common AE

No Clinically Significant trends related to safety

Ad-hoc analyses demonstrate dose dependent response through 4 mg

Patient symptoms and outcomes (GSRS and PGWBI) provided efficacy signals that support IP observations and will help with patient selection for the Phase IIb clinical trial Study design was underpowered for the Day 14 vs Day 0 IP ratio endpoint

TABLE 17

GSRS By Syndrome, Aggregate Groups - Multiple dose POC study - CLIN1001-004(Phase IIa) Total Dimension Score Change from Day 0 to Day 14

| | P/G | P/P & 8 mg/P | 0.25/1/4/8 mg |
|---|---|---|---|
| Diarrhea | 1.83 | −0.80* | 0.70 |
| p value | | .040* | 0.256 |
| Indigestion | 4.50 | −0.50 | 1.05 |
| p value | | 0.008** | 0.009* |
| Constipation | 1.17 | 1.10 | 0.76 |
| p value | | 0.949 | 0.601 |
| Abdom. Pain | 2.17 | −0.10 | 0.16 |
| p value | | 0.023* | 0.026* |
| Reflux | 1.00 | 0.90 | 0.08 |
| p value | | 0.905 | 0.068 |

*p < 0.05 with Dunnett's test
**p < 0.01 with Dunnett's test

REFERENCES

1. Fasano A. Regulation of intercellular right junctions by zonula occludens toxin and its eukaryotic analogue zonulin. Ann N Y Acad Sci. 2000; 915:214-22.
2. Fasano A. Intestinal zonulin: open sesame. Gut. 2001; 49:159-62.
3. Fasano A, Not T, Wang W, et al. Zonulin, a newly discovered modulator of intestinal permeability, and its expression in celiac disease. Lancet. 2000; 355:1518-19.
4. Wang W, Uzzau S, Goldblum S E, Fasano A. Human zonulin, a potential modulator of intestinal tight junctions. J Cell Sci. 2000; 113:4435-40.
5. Marinaro M, Di Tommaso A, Sergio U, Fasano A, DeMagistis M. Zonula occludens toxin is a powerful mucosal adjuvant for intranasally delivered antigens. Infect Immun 1999; 67:1287-91.
6. Marinaro M, Fasan A, DeMagisrtis M. Zonula occludens toxin acts as an adjuvant through different mucosal routes and induces protective immune responses. Infect Immun 2003; 71:1897-902.
7. Drago S, El Asmar R, Di Pierro M, Clemente M G, et al. Gliadin, zonulin, and gut permeability: effects on celiac and non-celiac intestinal mucosa and intestinal cell lines. Scan J Gastroenterol. 2006:41:408-19.
8. Fasano A, Uzzau S, Fiore C, Margaretten K. The enterotoxic effect of zonula occludens toxin on rabbit small intestine involves the paracellular pathway. Gastroenterol. 1997; 112:839-46.
9. Ventura A, Magazzu G, Greco L. Duration of exposure to gluten and risk for autoimmune disorders in patients with celiac disease. SIGEP Study Group for autoimmune disorders in celiac disease. Gastroenterol. 1999; 117:297-303.
10. Schuppan D. Current concepts of celiac disease pathogenesis. Gastroenterol. 2000; 119:234-42.
11. Norris J M, Barriga K, Hoffenberg E J, et al. Risk of celiac disease autoimmunity and timing of gluten introduction in the diet of infants at increased risk of disease. JAMA. 2005; 293:2343-51.
12. Clemente M G, De Virgiliis S, Kang J S, et al. Early effect of gliadin on enterocyte intracellular signaling in intestinal barrier function. Gut. 2003; 52:218-23.
13. National Institutes of Health. Consensus Development conference Final Statement dated Aug. 9, 2004. NIH consensus Development Conference on Celiac Disease. Bethesda, Md. Jun. 28-30, 2004.
14. Doig C J, Sutherland L R, Sandham J D, Fick G H, Verhoef M, Meddings J B. Increased intestinal permeability is associated with the development of multiple organ dysfunction syndrome in critically ill ICU patients. Am J Respir Crit Care Med. 1998 August; 158(2):444-51.
15. Van Heel D A, Hunt K, Greco L, Wijmenga C. Genetics in celiac disease. Best Pract Res Clin Gastroenterol. 2005; 19:323-39.
16. Monsour A J, De Bakker P I W, Alizadeh B Z, et al. Myosin IXB variant increases the risk of celiac disease and points toward a primary intestinal barrier defect. Nat Genet. 2005; 12:1032-41.
17. Palova-Jelinkova L, Rozkova D, Pecharova B, et al. Gliadin fragments induce phenotypic and functional maturation of human dendritic cells. J Immunol. 2005; 175:7038-45.
18. Anderson R P, Van Heel D A, Tye-Din J A, et al. T cells in peripheral blood after gluten challenge in coeliac disease. Gut. 2005; 54:1217-23.
19. Arrieta, M C, Bistritz, L and Meddings, J B. Alterations in intestinal permeability. Gut. 2006; 55; 1512-1520.

What is claimed is:

1. A method for treating celiac disease in a celiac patient on a gluten-free diet, comprising: administering to the luminal surface of the duodenum of the patient a peptide having the amino acid sequence of SEQ ID NO:15 (Larazotide Acetate), the peptide being administered at least three times daily prior to a meal so as to block persistent intestinal permeability and immune activation, wherein the peptide is administered in an oral dosage capsule comprising enteric-coated multiparticulate beads that are stable in gastric fluid but unstable in intestinal fluid so as to release peptide at the duodenum.

2. The method of claim 1, wherein the celiac disease is in remission.

3. The method of claim 1, wherein the patient has an anti-tissue transglutaminase (tTG) level of 10 EU or less.

4. The method of claim 1, wherein the administering step is for a period of at least two weeks.

5. The method of claim 1, wherein the peptide is administered about 15 minutes prior to a meal.

6. The method of claim 1, wherein the capsule comprises from 0.25 mg to 8 mg of the peptide.

7. The method of claim 6, wherein the capsule comprises about 1 mg of the peptide.

8. A method for treating a celiac patient on a gluten-free diet, comprising: administering to the patient for a period of at least two weeks, an oral dosage capsule comprising enteric-coated beads containing from 0.25 mg to 8 mg of Larazotide acetate, and formulated for delivery to the duodenum, the capsule being administered at least three times daily about 15 minutes prior to a meal, and the capsule comprising enteric-coated multiparticulate beads that are stable in gastric fluid but unstable in intestinal fluid so as to release peptide in the duodenum.

* * * * *

SEQUENCE LISTING

```
<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 1

Gly Arg Val Cys Val Gln Pro Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 2

Gly Arg Val Cys Val Gln Asp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 3

Gly Arg Val Leu Val Gln Pro Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 4

Gly Arg Val Leu Val Gln Asp Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 5

Gly Arg Leu Cys Val Gln Pro Gly
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 6

Gly Arg Leu Cys Val Gln Asp Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 7

Gly Arg Leu Leu Val Gln Pro Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 8

Gly Arg Leu Leu Val Gln Asp Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 9

Gly Arg Gly Cys Val Gln Pro Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 10

Gly Arg Gly Cys Val Gln Asp Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 11

Gly Arg Gly Leu Val Gln Pro Gly
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 12

Gly Arg Gly Leu Val Gln Asp Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 13

Gly Gly Val Cys Val Gln Pro Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 14

Gly Gly Val Cys Val Gln Asp Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 15

Gly Gly Val Leu Val Gln Pro Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 16

Gly Gly Val Leu Val Gln Asp Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 17

Gly Gly Leu Cys Val Gln Pro Gly
1               5

<210> SEQ ID NO 18
```

```
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 19

Gly Gly Leu Leu Val Gln Pro Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 20

Gly Gly Leu Leu Val Gln Asp Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 22

Gly Gly Gly Cys Val Gln Asp Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Zonulin antagonist

<400> SEQUENCE: 23

Gly Gly Gly Leu Val Gln Pro Gly
1               5

<210> SEQ ID NO 24
<211> LENGTH: 8
```

```
<212> TYPE: PRT
<213> ORGANISM: Artificial Sequence
<220> FEATURE:
<223> OTHER INFORMATION: Zonulin antagonist

<400> SEQUENCE: 24

Gly Gly Gly Leu Val Gln Asp Gly
1               5
```